(12) United States Patent
Gellman et al.

(10) Patent No.: US 10,596,384 B2
(45) Date of Patent: Mar. 24, 2020

(54) METHOD AND SYSTEM FOR BONE REGENERATION

(71) Applicant: Garwood Medical Devices, LLC, Buffalo, NY (US)

(72) Inventors: Gregg Gellman, Getzville, NY (US); Brian Peterson, Cumberland, RI (US); Merry Riehm-Constantino, Buffalo, NY (US); John Fournier, Lockport, NY (US); Edward Furlani, Lancaster, NY (US); Amy Hangen, Clarence, NY (US)

(73) Assignee: Garwood Medical Devices, LLC, Buffalo, NY (US)

( * ) Notice: Subject to any disclaimer, the term of this patent is extended or adjusted under 35 U.S.C. 154(b) by 189 days.

(21) Appl. No.: 15/927,240

(22) Filed: Mar. 21, 2018

(65) Prior Publication Data

US 2019/0290925 A1  Sep. 26, 2019

(51) Int. Cl.
| | | |
|---|---|---|
| *A61N 1/40* | (2006.01) | |
| *A61N 1/372* | (2006.01) | |
| *A61N 1/32* | (2006.01) | |
| *A61N 1/375* | (2006.01) | |
| *A61N 2/02* | (2006.01) | |
| *A61N 1/36* | (2006.01) | |

(52) U.S. Cl.
CPC .............. *A61N 1/40* (2013.01); *A61N 1/326* (2013.01); *A61N 1/375* (2013.01); *A61N 1/37223* (2013.01); *A61N 2/02* (2013.01); *A61N 1/36014* (2013.01)

(58) Field of Classification Search
CPC ...... A61N 1/40; A61N 1/37223; A61N 1/326; A61N 1/375
USPC ............................................. 607/51
See application file for complete search history.

(56) References Cited

U.S. PATENT DOCUMENTS

| | | |
|---|---|---|
| 6,261,221 B1 | 7/2001 | Tepper et al. |
| 2010/0210893 A1 | 8/2010 | Pilla |
| 2011/0004261 A1 | 1/2011 | Sham et al. |
| 2011/0196371 A1 | 8/2011 | Forsell |

*Primary Examiner* — Brian T Gedeon
*Assistant Examiner* — Philip C Edwards
(74) *Attorney, Agent, or Firm* — Stadler IP Law PLLC

(57) ABSTRACT

A method and system for bone regeneration is provided that includes an electrical stimulation system for the purpose of accelerating the process of bone healing. The electrical stimulation system includes a coil and a capacitor such that when the coil is powered a pulsed electromagnetic field is generated to accelerate healing. There are also implantable medical devices that include inserts such as an elbow insert. The elbow insert includes or is formed with a repeater coil and a device capacitor, such that when the coil is powered the device coil is powered and delivers a repeater pulsed electromagnetic filed to the surrounding bone. This inductive coupling provides for treatment by both the coil and the repeater coil to accelerate bone healing. The insert may be embodied so it can be used in connection with a plurality of different implantable medical devices.

21 Claims, 13 Drawing Sheets

METHOD AND SYSTEM FOR BONE REGENERATION

FIELD OF INVENTION

This invention is directed to a method for bone regeneration that entails the use of an electrical stimulation system for the purpose of accelerating the process of bone healing.

BACKGROUND OF INVENTION

A problem associated with bone injuries, for example broken bones, is that healing bone tissue takes a long time. Bones may take anywhere from three to six weeks to heal. The long healing process may result in the patient prematurely moving as normal only to re-fracture the bone. In addition, the longer a bone takes to heal, the higher the probability of a patient developing an ailment related to the bone injury.

Thus, there is a need to accelerate the healing process of bones with a system that is easy to use and produces enhanced healing. It would be desirable if a system were provided that safely and reliably speeds up the healing process, for example while the patient wears an orthotic, bandage or casting.

SUMMARY OF THE INVENTION

There is provided a bone regeneration system that incorporates a support, for example an orthopedic device such as an orthopedic brace or cast, electronics stimulation for improving wound healing, while also delivering energy to an implantable device. The orthopedic device provides electrical stimulation (hereinafter referred to as ES) therapy in the form of inductively coupled pulsed electromagnetic field (hereinafter referred to as PEMF) therapy and may include capacitively coupled (hereinafter referred to as CC) electric field therapy to accelerate the bone healing process.

A method of bone regeneration is provided that entails the use of the bone regeneration system. The bone regeneration system includes the support that may be embodied as an orthopedic device, a bandage like support, or an orthopedic casting that supports an injured body part. The support houses or has mounted thereon an electrical stimulation system (hereinafter referred to as ESS). The ESS includes a coil or coils that generate a PEMF for electrical stimulation therapy (hereinafter referred to as ES therapy), an onboard power sources and/or a wireless power transfer system to power the ESS, biometric sensors and electronic circuits that enable programmable operation of the ESS for customized therapy and transmission of sensor data for monitoring the therapeutic effect and patient progress and compliance in the application of the therapy. Patient and treatment information can be encrypted, sent wirelessly, and stored either on local data systems and/or the cloud for review by a clinician. The ESS contained in or otherwise mounted on the support can be powered using a remote wireless power transfer system.

The bone regeneration system may also include the following subsystems:

(a) an implantable non-metallic elbow insert, knee spacer, spine insert, or hip insert or spacer, or non-metallic bushing, which contains a conductive repeater coil or multiple coils tuned to the frequency generated by the ESS, to promote bone regeneration locally, in vivo, at the site of the bone to be treated. The implanted elbow insert, knee spacer, spine insert, or hip insert can be placed in more than one location and can be located in an area that is closer to where the bone growth is needed.

(b) an active bandage that provides for wound healing to promote the healing of incisions or chronic wounds on the body. The active bandage contains a more compact version of the ESS, with all the electronic control circuitry, sensing and communication devices stated herein. While the ESS mounted on the support and the active bandage ESS have similar components, they have different operating parameters (e.g. voltage profiles) to promote bone and wound healing, respectively, as is well known by one having ordinary skill in the art. The active bandage can have an on board power source or receive wired or wireless power from the ESS on the support. The active bandage ESS can also provide wireless power to, and control of, the implanted ESS as described in (a) above.

(c) a portable device that can provide wireless power to the ESS mounted on the support, brace, or bandage.

The ESS contained in the support can also power and control the implanted ESS and/or ESS in the active bandage.

BRIEF DESCRIPTION OF THE DRAWING FIGURES

Figure 13:
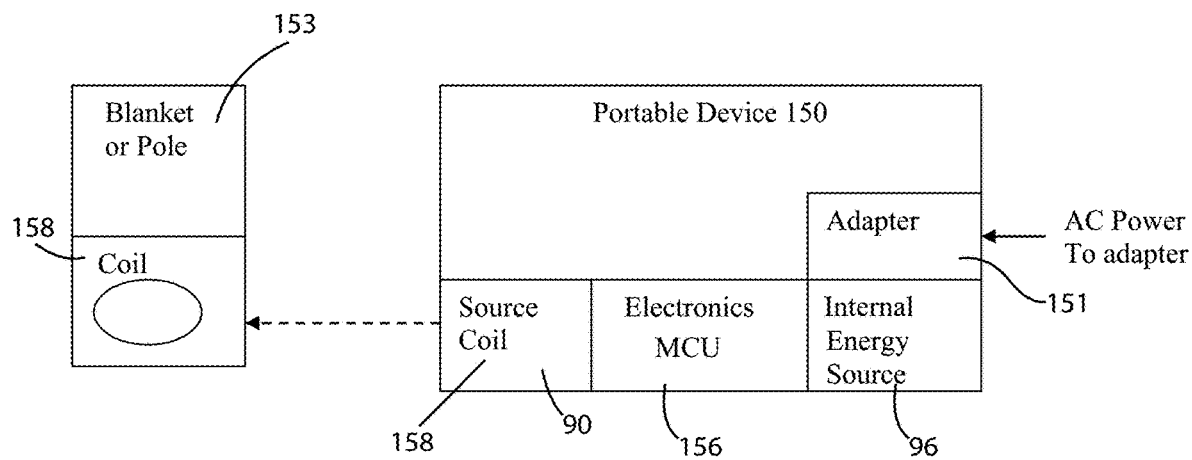
Figure 14:
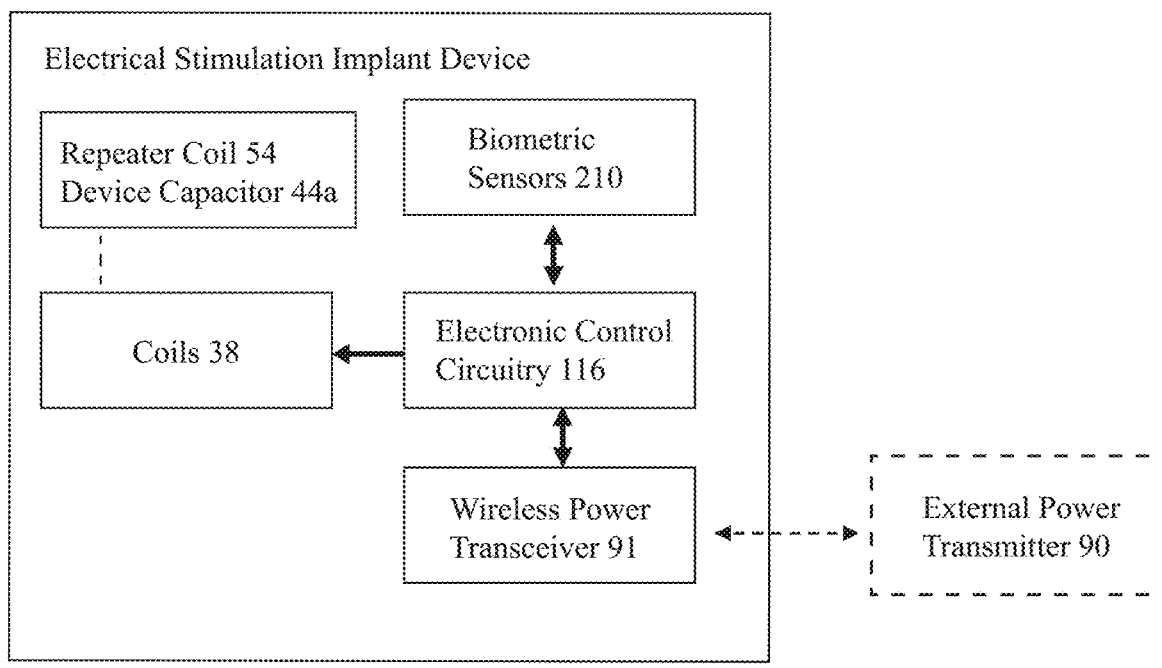

FIG. 13 diagrammatically depicts a portable device for use in connection with the bone regeneration system FIG. 14 is a block diagram depicting remote powering of implanted medical device.

FIG. 15 is an expanded view of an active bandage having with an electrical stimulation system.

Figure 16:
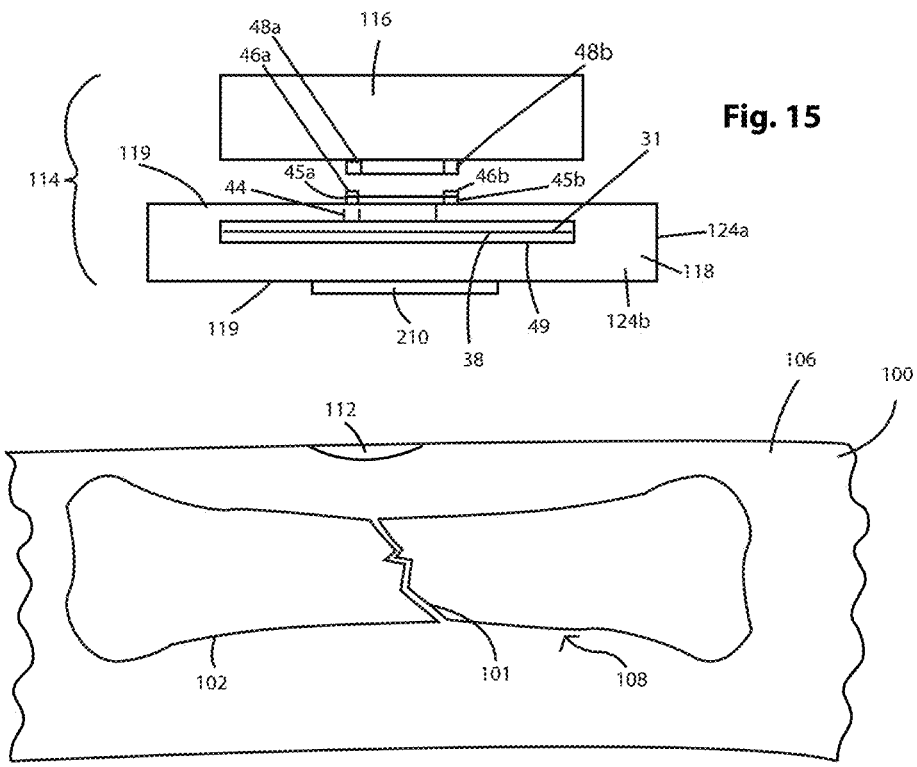

FIG. 16 is a sectional view of a broken bone prior to the active bandage being placed on skin where the broken bone is located.

DESCRIPTION

At the outset, it is to be understood that like reference numerals are intended to identify the same structural elements, portions or surfaces consistently throughout the several drawing figures, such at elements, portions or surfaces that may be further described or explained by the entire written specification, of which this detailed description is a part.

A bone regeneration system 10 is described herein, and the description of the features and embodiments thereof is generally include as follows:

1. A bone regeneration system with structural and functional description;
2. The supports FIGS. 1-10;
3. Inductive Coupled Electrical/Magnetic Stimulation;
4. A wireless energy source;
5. Multiple sensor selection (FIG. 11);
6. User interface and the cloud;
7. Portable device FIG. 13; and,
8. Implantable tuned coil.

1. Bone Regeneration System with Structural and Functional Description

Figures 1, 1A:
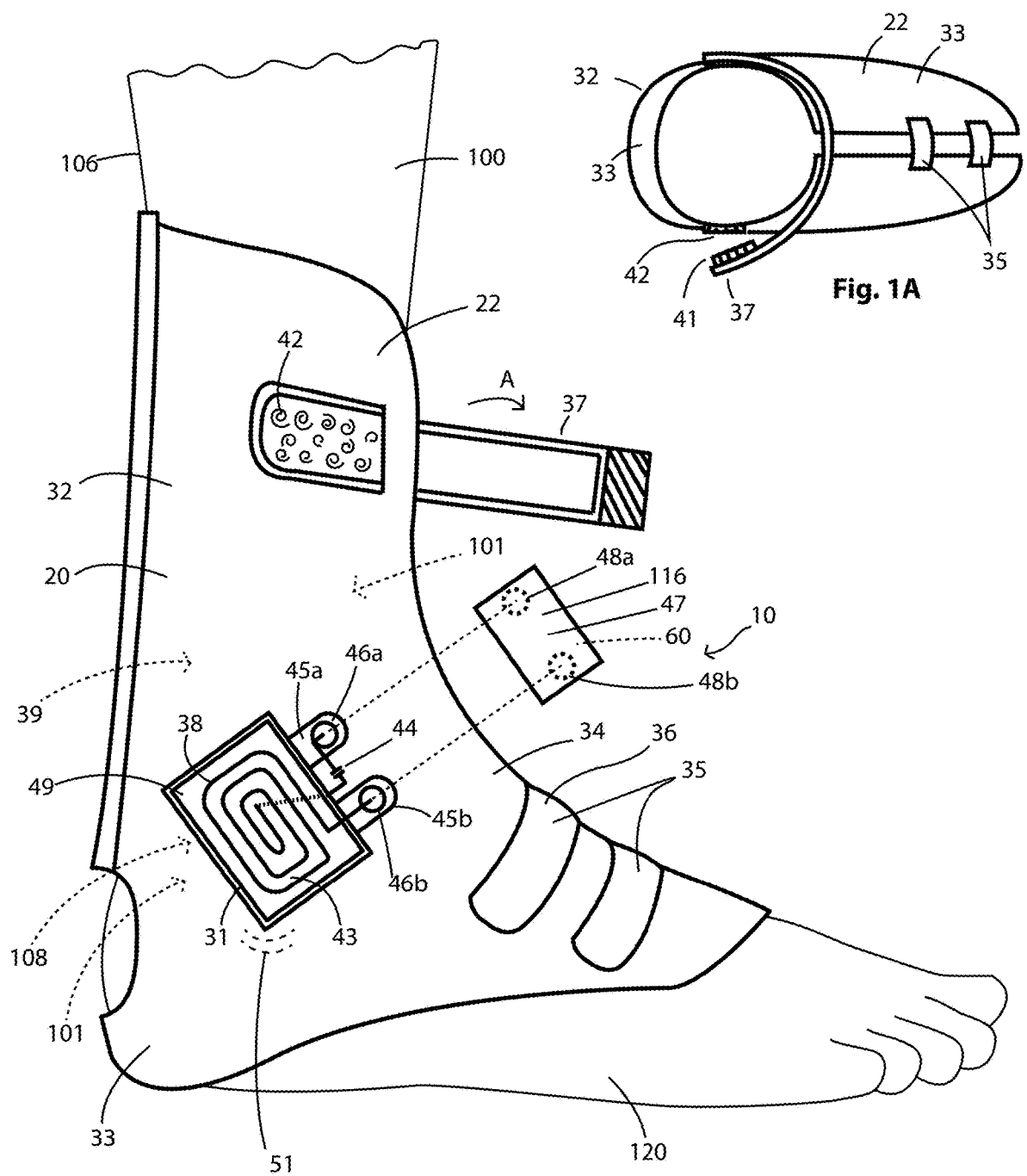
FIG. 1 is a front view of an ankle orthotic having an EES and being worn by a patient.
FIG. 1A is a top view of the ankle orthotic.
Figure 2:
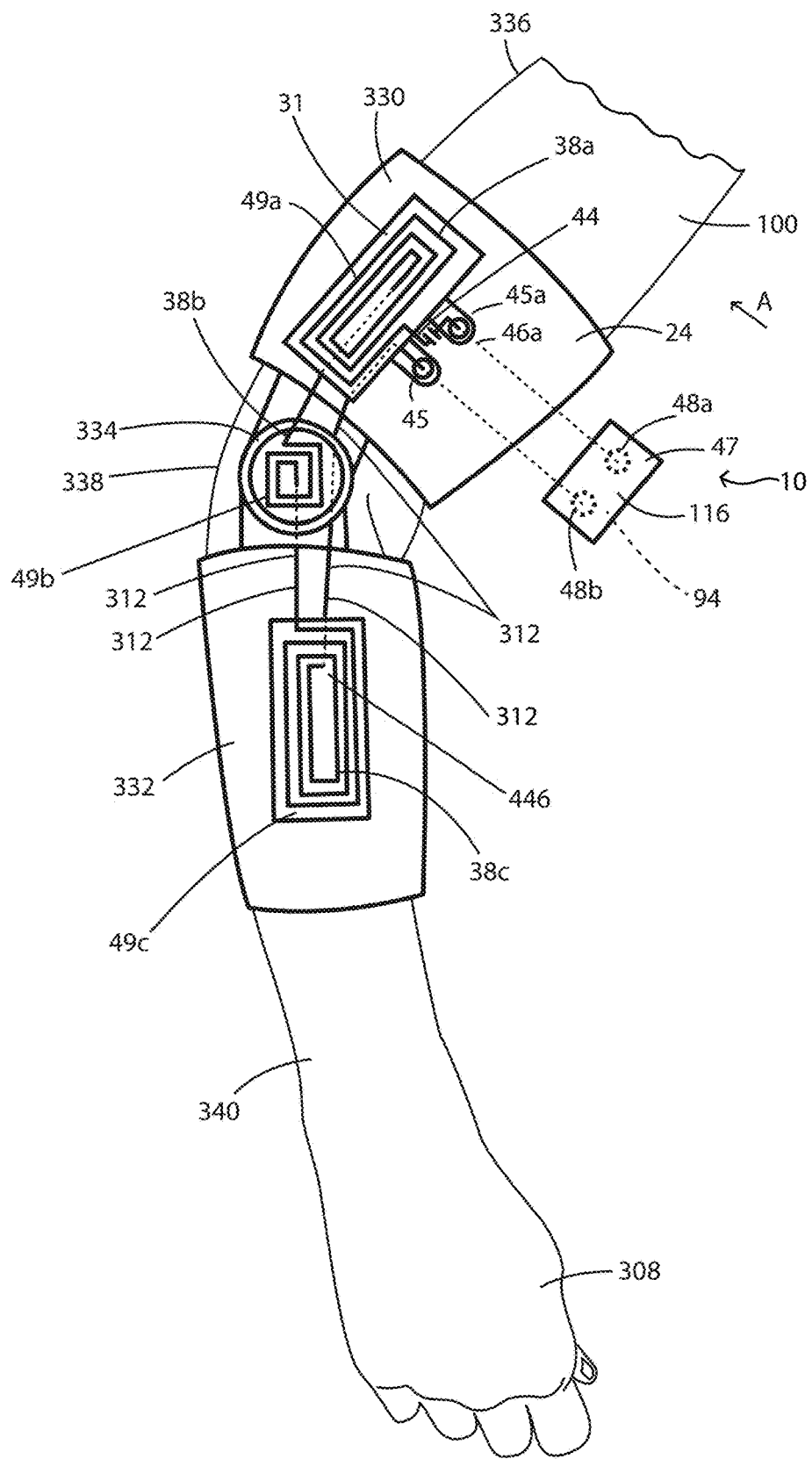
FIG. 2 is a front view of an elbow orthotic having an EES worn by the patient.
Figure 3:
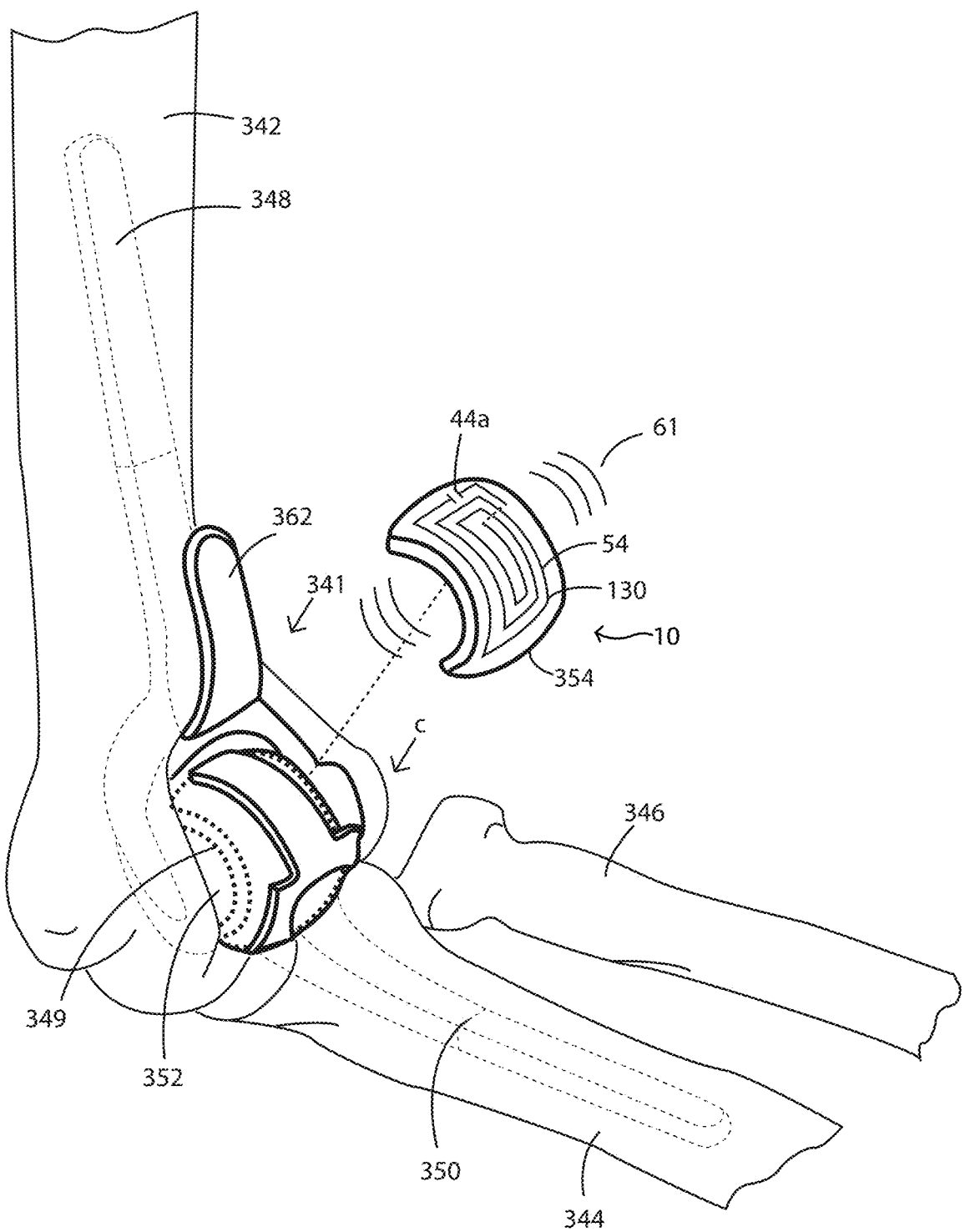
FIG. 3 is an exploded view showing an implantable elbow insert having an elbow insert having a repeater coil that is wired to a device capacitor and is inductively powered by the EES shown in FIG. 2 and positioned between the humerus and ulna bones.
Figure 4:
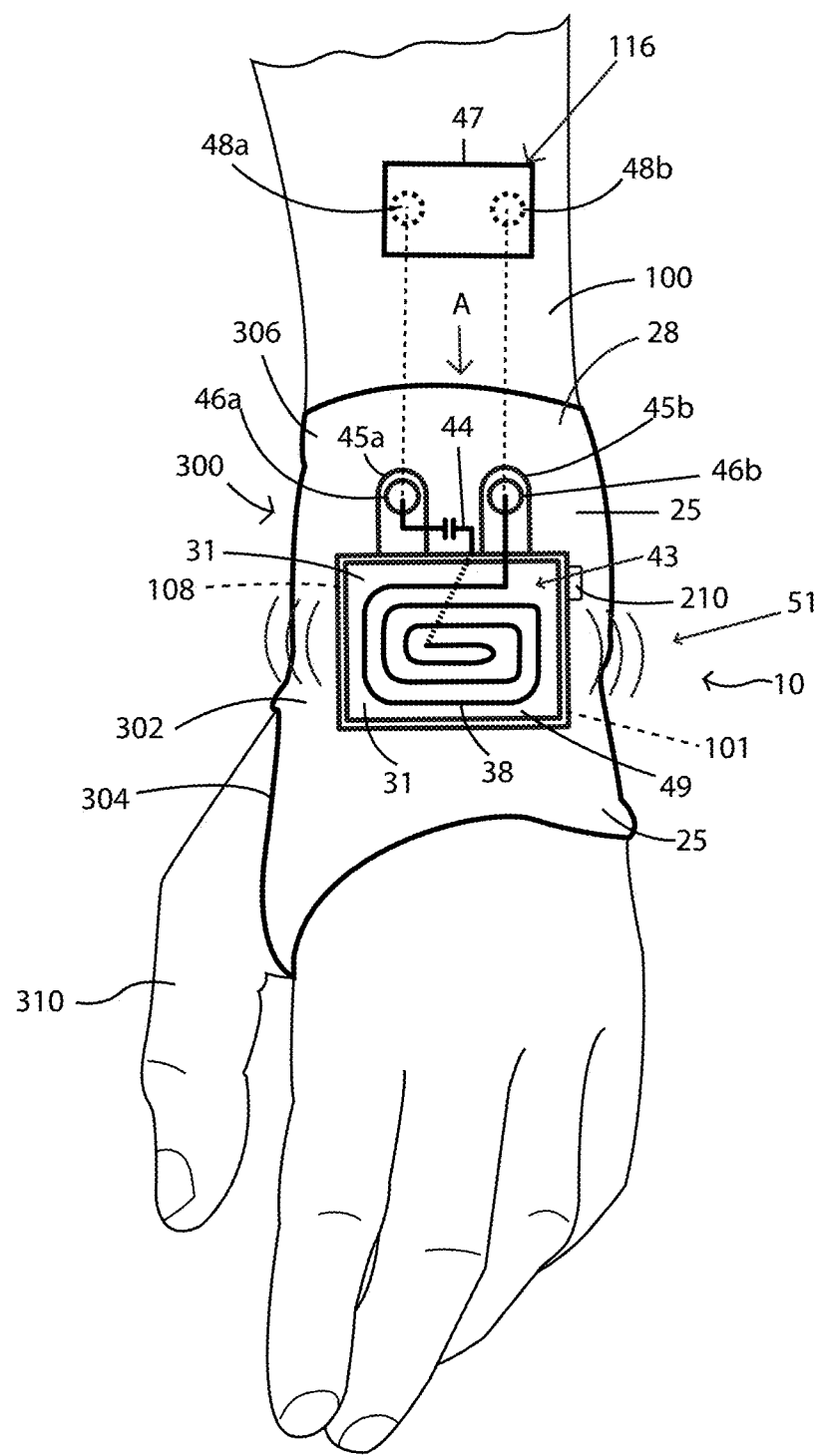
FIG. 4 is a top view of a wrist orthotic having an EES and being worn by the patient.
Figure 5:
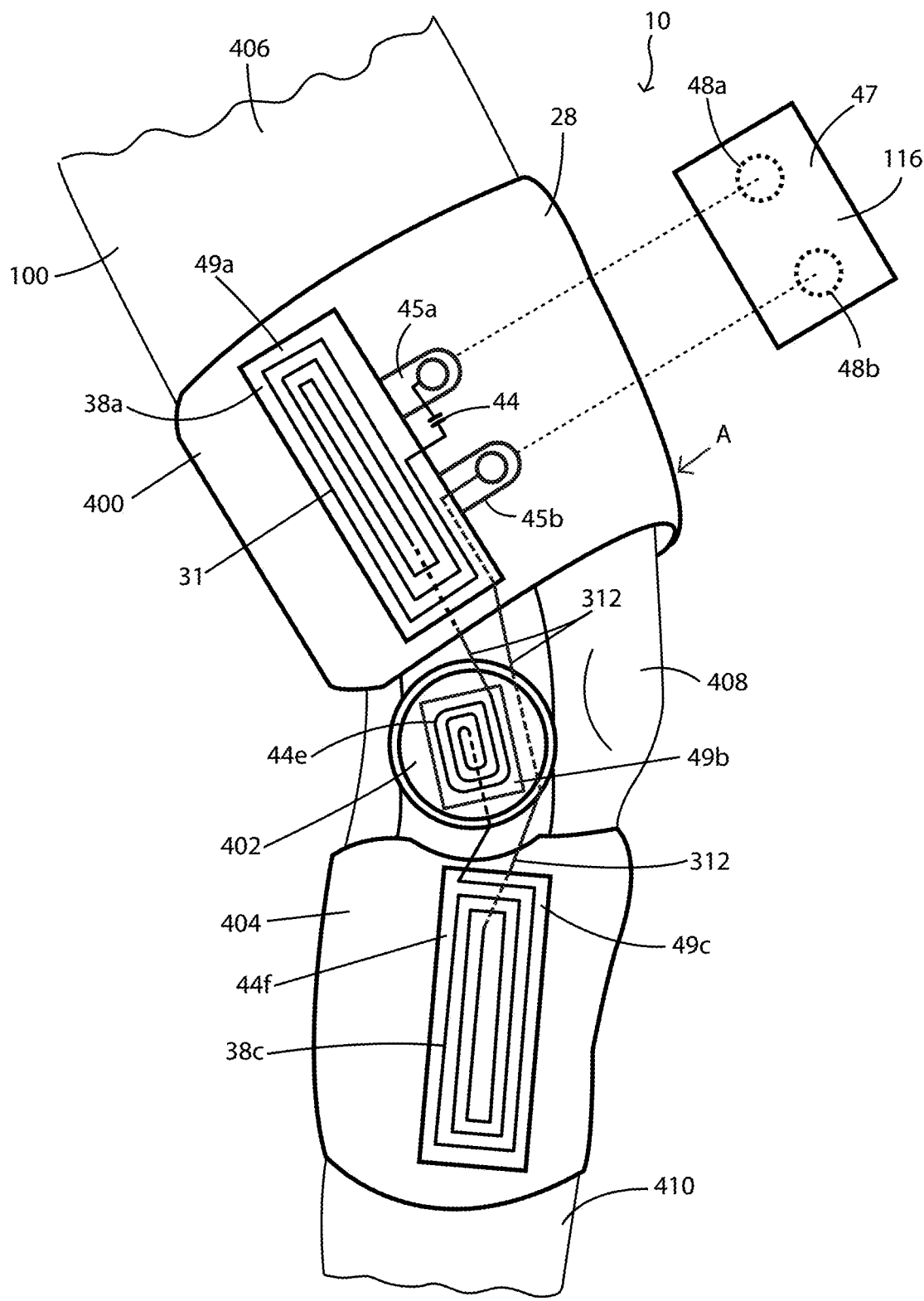
FIG. 5 is a front view of a knee orthotic having an EES and being worn by the patient.
Figure 6:
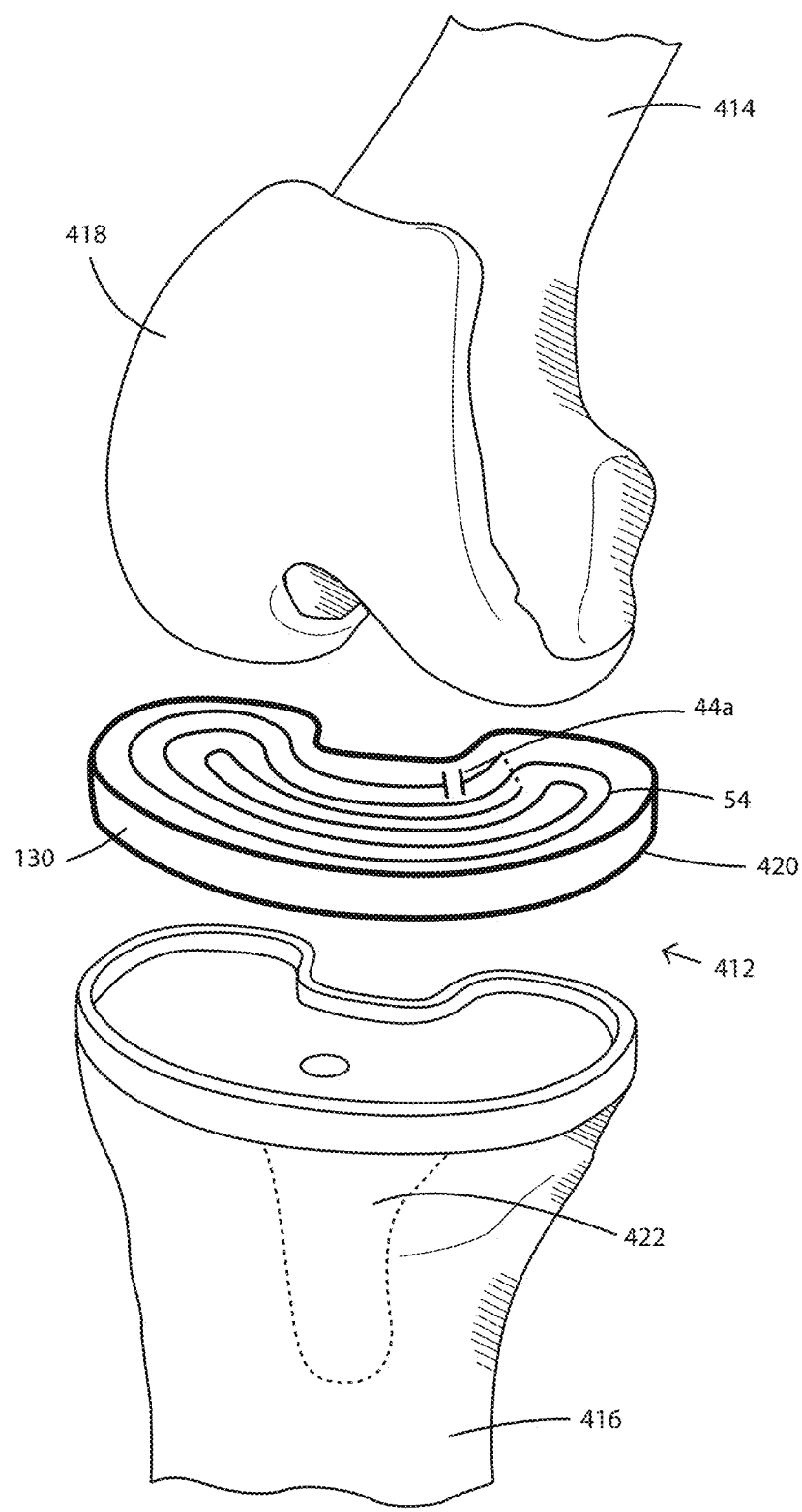
FIG. 6 is an expanded view of showing an implantable knee spacer having a repeater coil and device capacitor, and the knee spacer coil is inductively powered by the EES shown in FIG. 5 and positioned between the tibia and fibia bones.
Figure 7:
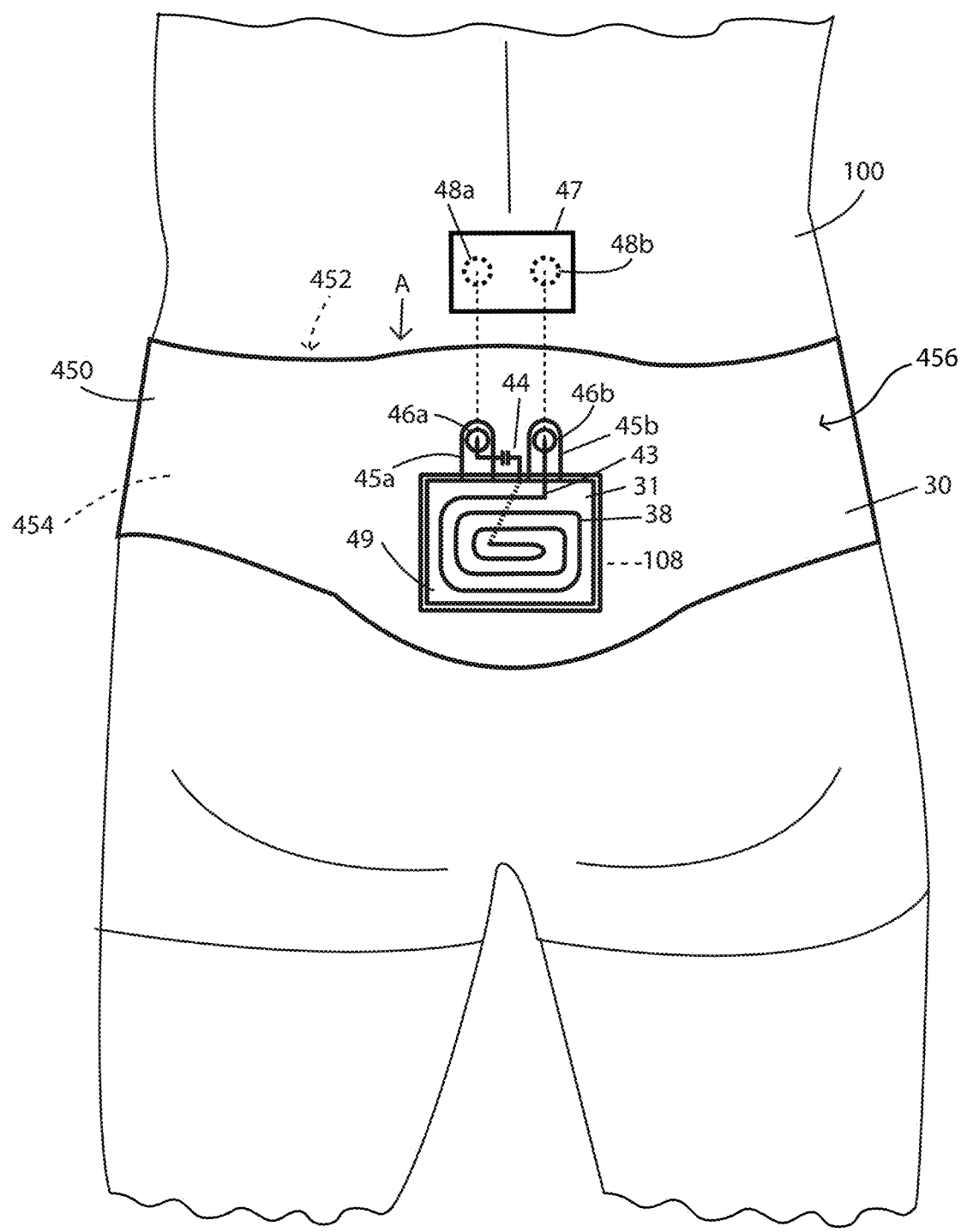
FIG. 7 is a front view of a spine orthotic having an EES and being worn by the patient.
Figure 8:
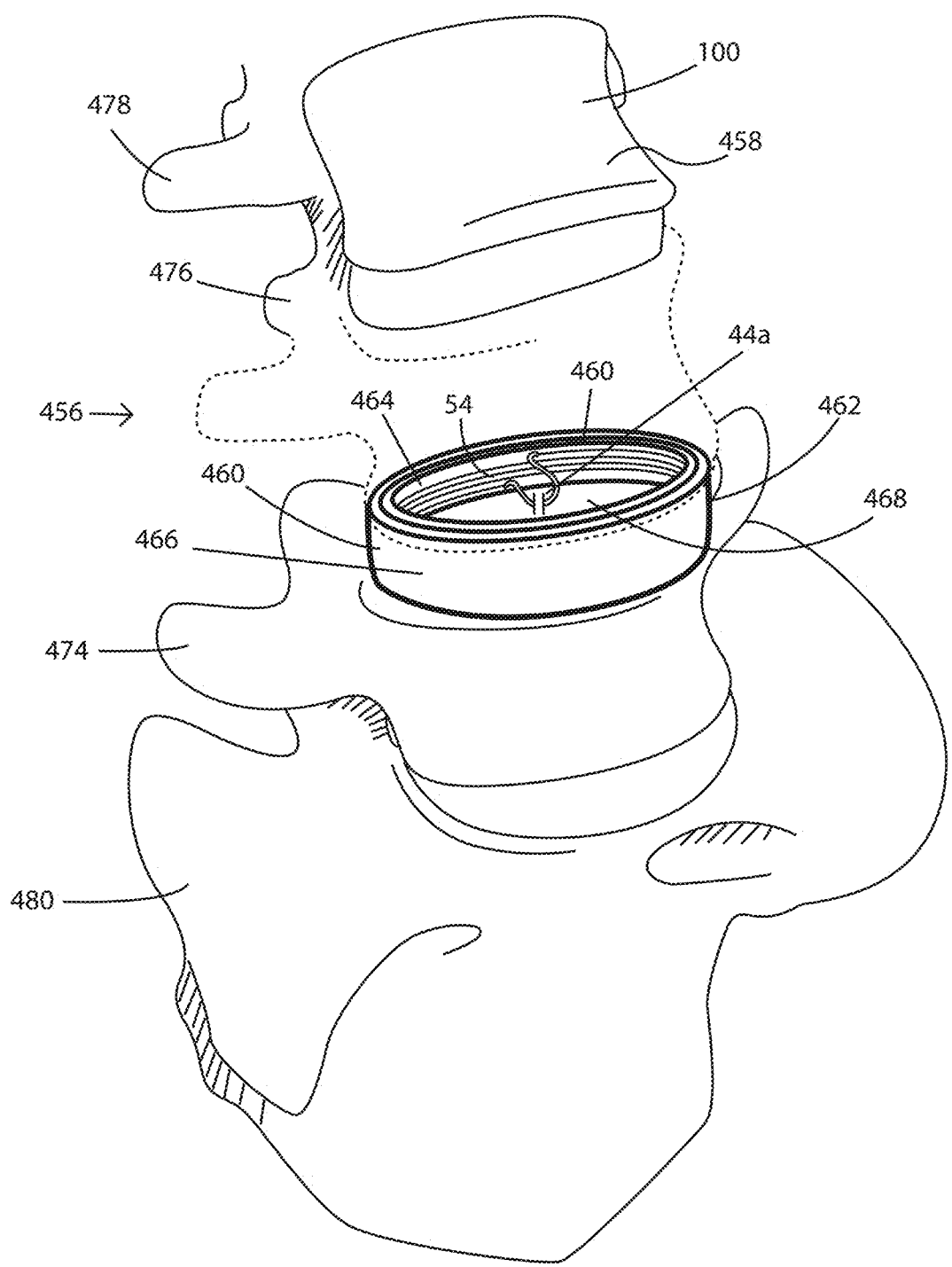
FIG. 8 is front view showing an implantable spine insert having a repeater coil that is cylindrical and wired to a device capacitor that is inductively powered by the EES shown in FIG. 7 and positioned between vertebrae.
Figure 9:
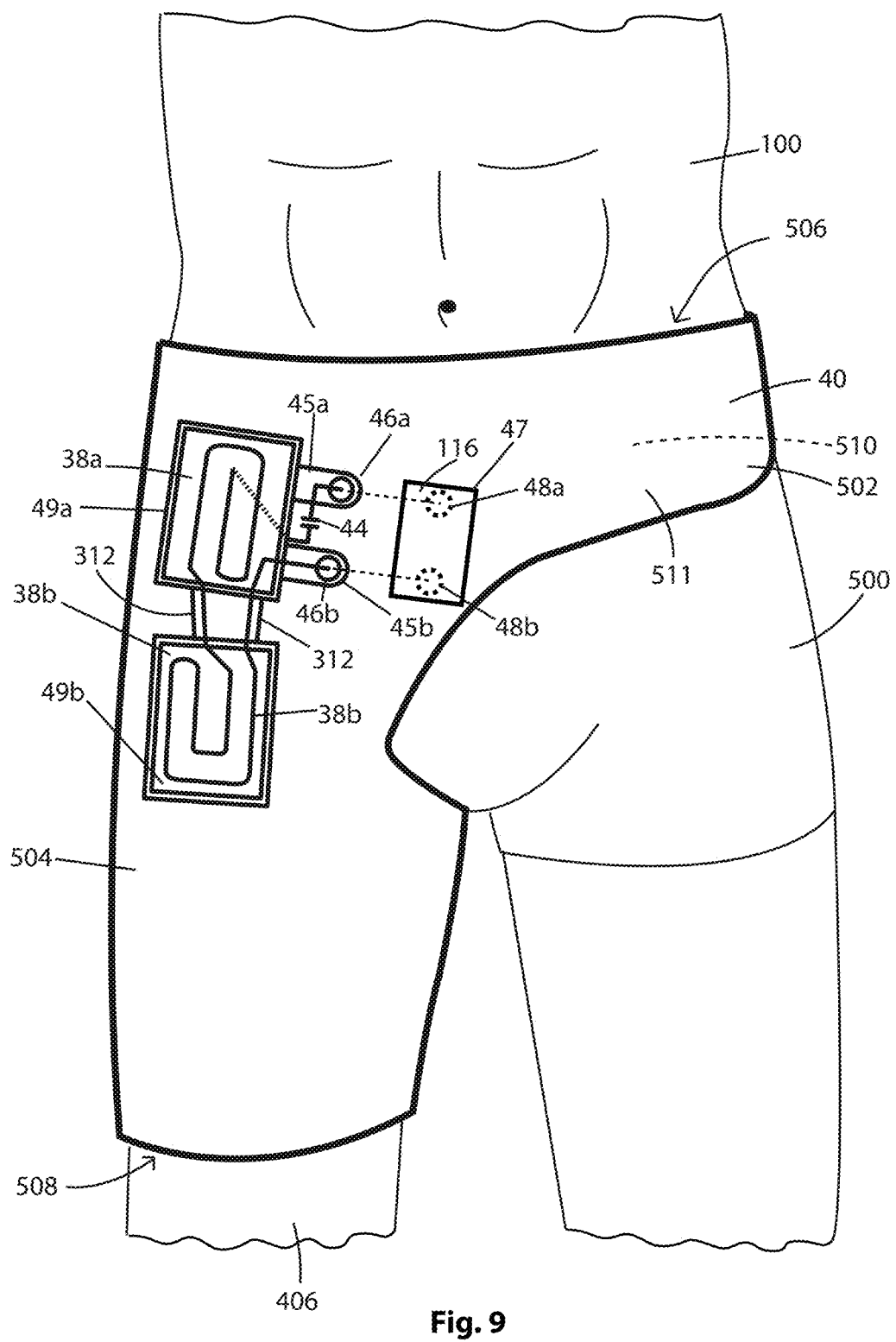
FIG. 9 is a front view of a hip orthotic having an EES and being worn by the patient.

In FIGS. 1-10 there are shown embodiments of the bone regeneration system 10 that includes an electrical stimulation system 116 (hereinafter referred to ESS 116) and shown in FIG. 11, and in another embodiment further includes a support 20 that supports the ESS 116. The ESS 116 is capable of healing bone 107 with a pulsed electromagnetic field or fields 50 (hereinafter sometimes referred to as PEMF 50) and shown for example in FIG. 4. The support 20 can be variously embodied and is embodied as an ankle orthotic 22 as shown in FIGS. 1 and 1A, an elbow orthotic 24 as shown in FIG. 2, a wrist orthotic 25 shown in FIG. 4, a knee orthotic 28 as shown in FIG. 5, a spine orthotic 30 as shown in FIG. 7, and a hip orthotic 40 as shown in FIG. 9. The EES 116 described herein can be used in connection with these orthotics and other orthotic devices now known or developed in the future.

Ankle

Figure 11:
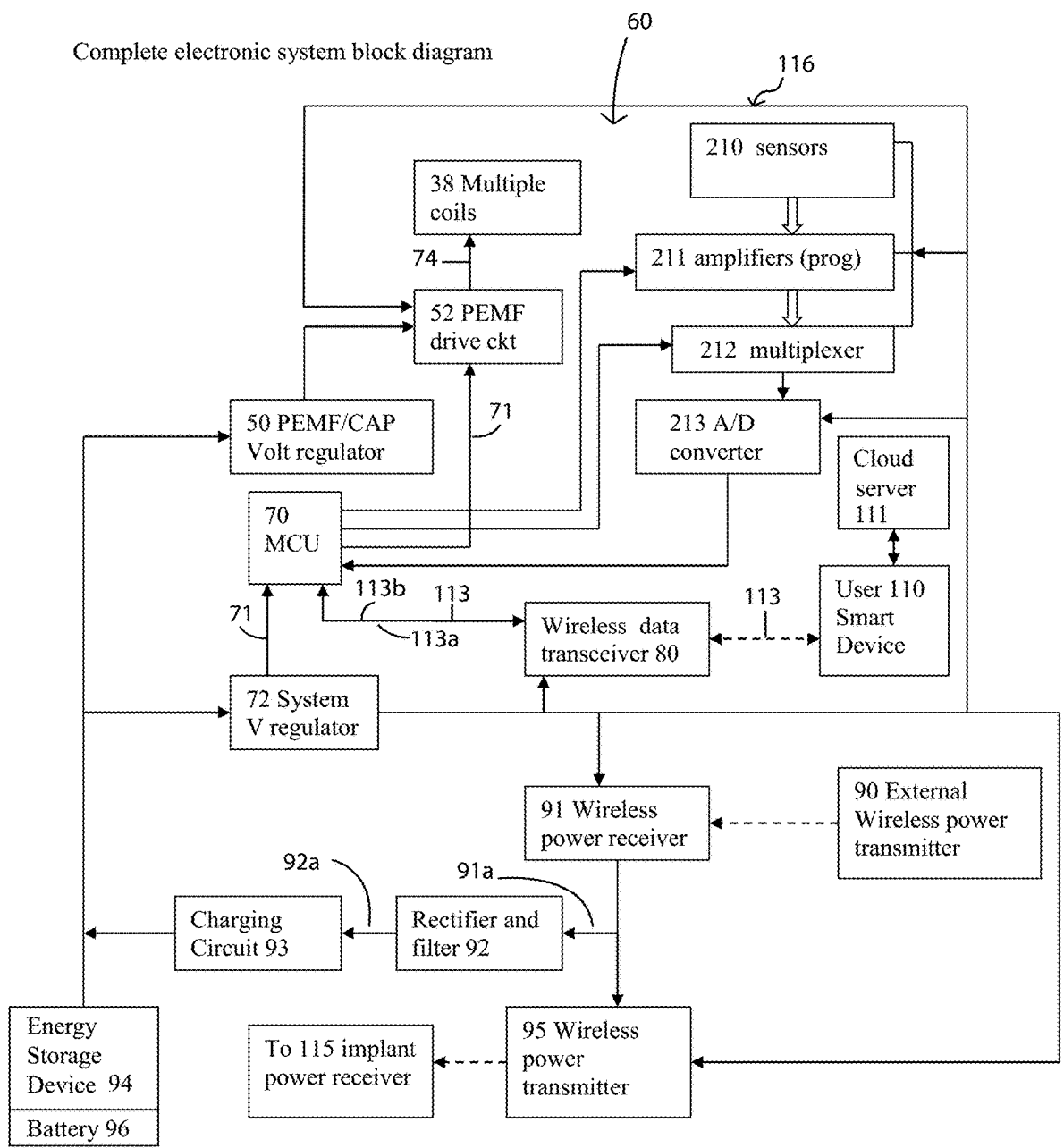
FIG. 11 is a system diagram depicting the bone regeneration system electronics for use in the bone regeneration system.

Turning now to FIGS. 1 and 1a there is the support 20 that is in the form of an ankle orthotic 22 that supports the ESS 116 and the ESS 116 includes system electronics generally designated by reference number 60 in FIG. 11 and to be described in greater detail presently. The ankle orthotic 22 has an ankle portion 32 that extends to a heel portion 33 and to a top of the foot portion 34. The ankle orthotic 22 also has straps 35 such that it can be fitted on the foot 120 and around the ankle 39 of a patient 100 and secured in place. In one embodiment the straps 35 are elastic bands 36. The ankle orthotic 22 also has an adjustment strap 37 that allows the ankle orthotic 22 to be adjusted relative to the ankle 39 of the patient 100. The adjustment strap 37 is mounted on the ankle portion 32 and the adjustment strap 37 has loop portion 41 as shown in FIG. 1A. A hook patch 42 is mounted on the ankle portion 32 such that when the ankle orthotic 22 is in the desired position the loop portion 41 can be secured to the hook patch 42 to hold the ankle orthotic 22 in place.

The EES 116 includes a coil assembly 31 having a coil 38, a capacitor 44, and a base 49 on which the coil 38 and capacitor 44 are mounted. The coil 38 and capacitor 44 form a LC circuit 43 as is well known to those having ordinary skill in the art. The coil 38 may be about five (5) millimeters thick, but may have other thicknesses in other embodiments. The EES 116 also includes an electronics housing 47 for housing the system electronics 60 of the EES 116. The base 49 of the coil assembly 31 is mounted on the ankle portion 32 of the ankle orthotic 22 as shown in FIG. 1, and the coil assembly 31 has first and second tabs 45a, 45b that extend from the base 49. First and second male snap components 46a, 46b, respectively, are mounted on the first and second tabs 45a, 45b, and as shown the first and second mail snap components 45a, 45b are wired to the capacitor 44, and the second male snap component 45b is wired to the coil 38. Mounted on the electronics housing 47 are first and second female snap components 48a, 48b, respectively, that are capable of being snap fitted to the first and second male snap components 46a, 46b, respectively such that the coil 38 electrically connected to and under the control of the master control unit 70 (to be described presently) shown in FIG. 11. The EES 116 also has an energy storage device 94 as shown in FIG. 11, such that when the first and second male snap components 46a, 46b are snapped fitted to the first and second female snap components 48a, 48b electric power delivered from an energy source 94 (see FIG. 11) is capable of flowing through the coil 38 and charging the capacitor 44. When the EES 116 causes current to be supplied to the coil 38 a pulsed electromagnetic field 51 (hereinafter sometimes referred to as PEMF 51) is generated that permeates the ankle 39 of the patient 100 at the location where he or she has a wound area (indicated by dashed reference line 108 in FIG. 1), and permeates a fractured or broken bone 101 (indicated by dashed reference line 101 in FIG. 1) that is in need of treatment. In other words, the PMEF 51 stimulates the healing of the broken bone 101 and can stimulate healing of surrounding tissues. The use of PEMF 51 therapy to treat broken bones is well known to those having ordinary skill in the art and therefore it not described in greater detail herein.

There may be a plurality of coils 38 in other embodiments that are wired to one another. The coils 38 are supported on the support 20 that is embodied as the ankle orthotic 22 described above, and as will be described presently the elbow orthotic 24, the wrist orthotic 26, the knee orthotic 28, a spine orthotic 30, or a hip orthotic 40. The PEMF 51 is produced or generated by the coil 38 or multiple coils 38 that are driven by the PEMF drive circuit 52 (FIG. 11). The outcome is an induced secondary electrical field produced in the bone broken bone 101. Both the characteristics of the applied magnetic fields and the biological properties of the surrounding tissues 105 and broken bone 101 influence the induced secondary electrical field as is well known to those having ordinary skill in the art. The PEMF drive circuit 52 enables the PEMF 51 to be varied in amplitude, frequency, pulse mode and wave form etc. The PEMF 51 can be produced to generate magnetic fields of 0.1-20 G within tissue to produce voltage gradients of 1-100 mV/cm as is well known.

The PEMF drive circuit 52 requires a regulated voltage input (that may be the same or different) provided by PEMF voltage regulator 50 shown in FIG. 11. The energy source 94 provides a source voltage level to the PEMF voltage regulator 50 and a system voltage regulator 72. The energy source 94 can be a battery 96 or a rechargeable battery, or capacitor storage.

The PEMF signal or field 51 is generated at a specific frequency and is transmitted into the patient 100, but as it travels through the patient 100 the signal loses some of its strength and also disperses to a larger area. The pulsed electromagnetic magnetic field 51 produced by the coil 38, shown in FIG. 1, is most dense at the coil 38 and decreases and loses strength as it travels through the patient 100. In an implantable medical device 130 (to be described presently) in order to direct the pulsed electromagnetic field 51 concentration into an implant coil referred to herein as a repeater coil 54 herein, for example the elbow insert 354 shown in FIG. 3 has a repeater coil 54 wired to a device capacitor 44*a*. The repeater coil 54 is tuned to the same frequency repeats the wireless signal it receives from the coil 38. This repeating is formed from the fact that this coil repeater 54 has a current induced on it from the PEMF 51 generated by the coil 38. This in turn causes a repeater PEMF 61 magnetic field to form around the repeater coil 54 (as indicated in FIG. 3). As a result the magnetic field will be dense around the repeater coil 54 and at the surface of the skin from the PEMF 51 being close. This allows for more PMEF 61 from the repeater coil 54 to exist at the break site in the broken bone 101, or surgical site. As will be described presently the repeater coil 54 can be placed inside of spacers and inserts that are used in connection with knee, elbow, hip and spine medical procedures. For a mixed frequency signal, such as a 27.12 MHz carrier signal and a 50 Hz modulation, one coil 38 can be tuned to 27.12 MHz and another, example the repeater coil 54 tuned at 50 Hz.

The repeater coil 54 is tuned by one of two methods. In one embodiment the repeater coil 54 can be designed in such away that the repeater coil's 54 self resonance matches the target. This can be done as the coil windings overlap causes a capacitance between the coil turns and thus can create a capacitance value that along with the inductance value of the coil will cause the coil to resonant at a frequency. This is called browser self-resonating coil and is known to having ordinary skill in the art.

In other embodiments the use of a series capacitance can be used to tune the coil whose value satisfies the following equation:

$$f = \frac{1}{2\pi \times \sqrt{L} \times C}$$

where f is the resonant frequency,

L is the inductance of the coil, and,

C is the total capacitance in series with the coil.

For knee, elbow, hip and spine medical applications the repeater coil (or coils) 54 may be located in the spacers, inserts or bushing (to be described presently) between the components of the implantable medical device 130. Additional repeater coils 54 can be placed around the implantable medical device 130 to further direct the repeater PEMF 61, but the repeater coil 54 needs to be electrically isolated from the implantable medical device 130, for example if the implantable medical device 130 is made of metal, then the repeater coil 54 has to be electrically isolated from the implantable medical device 130.

For spine fusion application of the various bones 101 that make up the spine, the repeater coil 54 can be embedded in the area in which bone graph is placed on the bone or in a 460 spine insert (shown in FIG. 8 and to be described presently) is placed on the bone 101 is being encouraged to grow. In virtually all cases, the repeater coil 54 is made of biocompatible material 132 or encased in a biocompatible material 132 and such that it does not need to be removed after treatment of the patient has been completed.

As shown in FIG. 11, the ESS 116 has an energy storage device 94 or may be powered by an external wireless power transmitter 95 that is not mounted on the support 20 and that transmits power to a wireless power receiver 91 located or mounted on the support 20. In the one embodiment, the external wireless power transmitter 95 and the wireless power receiver 91 are inductively coupled and operate in a resonant mode to optimize power transfer in a manner that is well known to those having ordinary skill in the art. The output 91*a* from wireless power receiver 91 is rectified and filtered by a rectifying and filtering component 92 and rectifying and filtering components are well known to those having ordinary skill in the art. The outputted rectified and filtered signal 92*a* from the rectifying and filtering component 92 can be used to power the ESS 116 directly or can be input to a charging circuit 93 that can charge the energy storage device 96 at a predetermined rate. A user smart device (USD) 110 transmits and receives wireless data 113 to and from a wireless data transceiver 80. A master control unit 70 (hereinafter referred to as MCU 70) receives the wireless data 113 from a wireless data transceiver 80, and the wireless data 113 includes data information 113*a* and parameters 113*b* required to program the stimulation therapy that satisfies the needs of the patient 100. MCU 70 sends out control signals 71 for programmed waveforms with prescribed frequency and duty cycle to the PEMF drive circuit 52, which in turn sends a conditioned signal 74 the coil or coils 38, respectively. Biometric sensors 210 are provided and controlled by the ESS 116 as shown in FIG. 11 to enable the monitoring of a patient 100 while he or she endures the healing progress. In one embodiment the biometric sensors 210 can be positioned and fixed on the skin 106 in proximity to the wound area 108, and the wound might be, for example an incision using sterile adhesive materials as is well known, to enable the biometric sensors 210 to monitor biometric data that can be used to access the state of the incision or wound and thus monitor the therapeutic progress being made by the patient 100. The biometric sensors 210 are wired to the ESS 116 for power and control.

Active Bandage

As shown in FIGS. 15 and 16, in another embodiment, the EES 116 provides for an active bandage 114 that also includes the biometric sensors 210 that may be placed on the skin 106 of the patient 100. The EES 116 used in the active bandage 114 includes a coil assembly 31 the same as described above and the coil assembly may include multiple coils 38. As shown in FIG. 16, the active bandage 114 has a padding layer 118 having opposed first and second padding surfaces 124*a*, 124*b* and adhesive 119 applied to both the first and second padding surfaces 124*a*, 124*b*, such that the ESS 116 is adhered to the padding layer 118, and the padding layer 118 is adhered to the skin 106. The active bandage 114 also has the previously described first and second tabs 45*a*, 45*b* on which are mounted first and second male snap components 46*a*, 46*b*, respectively, and the previously described first and second female snap components 48*a*, 48*b*, respectively. The coil assembly 114 may be disposed internal to the padding layer 118 as shown or mounted on the first padding surface 124*a*. The first and second male snap components 46*a*, 46*b* are snap fitted to the first and second female snap components 48*a*, 48*b* and the padding layer 118 is adhered to the skin 106 of the patient 100. The padding layer 118 covers and protects the wound area 108 to promote healing of the broken bone 101 and the coil 38 provides the PMEF 51 to promote healing of the broken bone 101. When the active bandage 114 is placed on the skin 106 over the broken bone 101, for example the broken bone 101 shown in FIG. 16, the coil 38 is powered it emits a PMEF 51 into the broken bone 101.

As shown in FIGS. 11, 15 and 16 the EES 116 is capable of acquiring and transmitting biometric sensor data transmission of biometric sensor data 212 associated with the wound 108, and the biometric sensor data 212 includes pH level data, pressure level data, temperature data, moisture data, humidity data and similar data. Biometric sensors are well known to those having ordinary skill in the art and are therefore not described herein in greater detail. In this embodiment, biometric the sensors 210 are integrated with and part of the active bandage 114. As shown in FIG. 11, the biometric data 212 signals from the biometric sensors 210 are input to programmable gain amplifiers 211 that are programmed by a the MCU 70. The MCU 70 selects which amplifier channel to input to the A/D converter 213 using an analog multiplexer 212. The MCU 70 sends the biometric sensor data 212 of the patient 100 out through the wireless data transceiver 80 to the user smart device 110 and then optionally sends the biometric sensor data 212 to a cloud server 111 for health care evaluation.

It is pointed out that the above described biometric sensor data 212 may be collected in the same manner for any of the embodiments described herein, for example, biometric sensor data 212 may be collected when the knee orthotic 28 or the spine orthotic 30 are used.

In another embodiment, the active bandage 114 may be powered wirelessly with an external power transmitter 90 that emits a resonantly tuned frequency that is received by the wireless power receiver 91 (mounted on the active bandage 114) that is resonantly coupled to the wireless power receiver 91, and this technique will be described in greater detail presently.

Implantable Medical Devices

As shown in FIGS. 3, 6, 8, and 10 in other embodiments the EES 116 is utilized to work in with implantable medical devices 130 as will be described presently. The implantable medical devices 130 are implanted in the patient 100 and the implantable medical device 130 is itself capable of promoting bone regeneration locally, in vivo, at the site of the broken bone 101 to be treated. The implantable medical device 130 includes a built-in (or is integrally formed) with a repeater coil 54 and device capacitor 44a that is designed such that it repeats and regenerates the wireless field generated by EES 116.

The support 20 supports the EES 116 and the coil 38 without adding complexity to the setup by a medical professional or the patient. The support 20 is administered to the patient 100, as it would normally be. The active bandage 114 described above can be used in connection with implantable medical devices 130 that have a repeater coil 54 and device capacitor 44a, such that the coil 38 of the active bandage 114 wirelessly powers the repeater coil 54.

Wireless Energy Source

This technique allows for power to be transferred over a distance of about one meter wirelessly. This allows a device that is plugged into a wall to transfer the power wirelessly to the support member 20 so that a power cord will not interfere with mobility of the patient. As shown in FIG. 11 there is an external power transmitter 90 that emits a resonantly tuned frequency that is received by the wireless power receiver 91 that is resonantly coupled to the wireless power receiver 91 to optimize efficient power transfer between the two as is well known by one having ordinary skilled in the, and that is located on the support member 20. From this point the received waveform can be rectified and filtered 92 and applied to charging circuit 93 for either a rechargeable battery or large capacitive energy source, or re-transmitted to an implanted power receiver 115 by wireless transmitter 95. It is noted that all the transmission coils and receiving coils used in this bone regenerating system 10 have quality factors greater than 100 for optimum energy transfer. Thus, this allows the EES 116 on the support 20 to be wirelessly powered.

Figure 12:
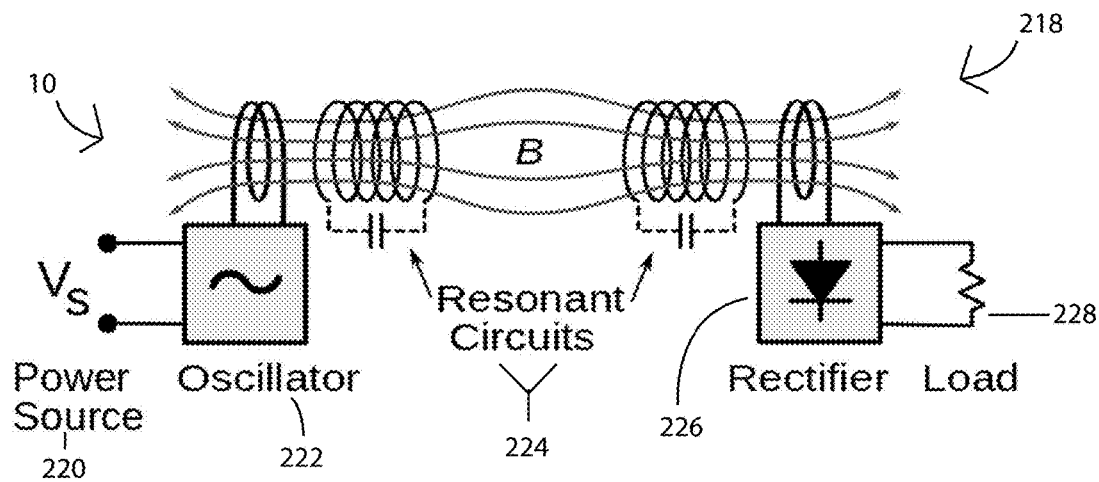
FIG. 12 is a circuit diagram depicting a resonant circuit showing wireless energy transfer.

For purposes of illustration, a typical resonant tank circuit transmitter and receiver arrangement is shown in FIG. 12 and indicated by reference number 218. The resonant tank circuit transmitter and receiver 218 have the following components: a power source 220, and oscillator 222, resonant circuits 224, a rectifier 226 and a load 228. This contains the source coil to transfer wireless energy to the broken bone 101. This pulsing magnetic field will not only help with the healing of bones 107, but it can also be utilized by an implanted medical device 130 having a coil for it to receive power. If the implantable medical device 130 is placed near the bone 107, then the ESS 116 can repeat the magnetic field around itself and thus provide magnetic stimulation of the bone 107 much closer to the treatment area.

Portable Wireless Device

In another embodiment shown in FIG. 13, there is a portable wireless device 150 that is capable of transferring power over a distance of one meter or more wirelessly. All of the electronics needed to monitor and generate the PEMF 51 are contained within the portable wireless device 150, and this is for simplicity of use by the user. The portable wireless device 150 is plugged into a wall socket (not shown) and has an adapter 151, or may have its own internal energy source, for example a battery 96. The portable wireless device 150 device also has portable device electronics 156 that allow are capable of powering an external wireless power transmitter 90 (FIG. 11) that can be embodied as a source coil 158. The source coil 158 can wirelessly transfer power to the wireless power receiver 91 that can be mounted on the support 20. This then allows the MCU 70, PEMF driver 52, coil 38 and other system electronics 60 to be powered such that PEMF 51 is delivered to the broken bone. This eliminates the need for power cords being attached to the patient 100, and allows the patient to have greater mobility. The portable wireless device 150 can be clipped to a pole or blanket commonly indicated by reference numeral 153 such that it is in out of the way position.

It is noted that the portable wireless device 150 adds a minimal amount of weight, because the portable wireless device 150 is not mounted on the support 20.

The bone regeneration system 10 can be used in a plurality of different treatments so long as there is a wound 112 to be treated and/or a bone 107 that needs help healing. The treatments for bone healing described herein can be using in connection with healing many bones 107, for example in the knee, hip, wrist, ankle, elbow, and spine as will be described presently. In addition, for all bones 102, the treatment can be used not just for stimulating the healing of a bone 102 that was broken, for example the bones 102 in the knee and hip, but also can be used to help speed the recovery from surgery where a bone 102 needed to be broken.

Orthotic Device Support

Wrist Orthotic

Turning now to the wrist orthotic 25 shown in FIG. 4, the wrist orthotic 25 is supported on the wrist 300 of the patient 100. The wrist orthotic 25 has a hand portion 302 that defines a thumb opening 304, and the wrist orthotic 25 may be made of a stiff hard material or as a cast 306 and in other embodiment may be made of a flexible breathable material such that it can be fitted over the hand 308 and thumb 310. The wrist orthotic 25 supports the EES 116. The EES 116 includes the coil assembly 31 that has the base 49 that supports the coil 38 and capacitor 44. The EES 116 also includes an electronics housing 47 that houses the system electronics 60. The coil assembly 31 is mounted on the hand portion 302 of the wrist orthotic 22 as shown, and the coil assembly 31 has first and second tabs 45*a*, 45*b* extending from it on which are mounted first and second male snap components 46*a*, 46*b*, respectively. The first and second mail snap components 45*a*, 45*b* are wired to the capacitor 44, and the second male snap component 45*b* is wired to the coil 38. Mounted on the electronics housing 47 are first and second female snap components 48*a*, 48*b*, respectively, that are capable of being snap fitted to the first and second male snap components 46*a*, 46*b*, respectively, such that the coil 38 and capacitor are under the control of the MCU 70. The EES 116 also has an energy source 94 as shown in FIG. 11, such that when the first and second male snap components 46*a*, 46*b* are snapped fitted to the first and second female snap components 48*a*, 48*b* (as indicated by the arrow designated A in FIG. 4) electric power is capable of flowing through the coil 38 and charging the capacitor 44. When the EES 116 causes current to be supplied to the coil 38 a PEMF 51 is generated that permeates the wrist 300 of the patient 100 at the location where he or she has a wound area (indicated by dashed reference line 108 in FIG. 1), and permeates a fractured or broken bone 101 (indicated by dashed reference line 101 that points in the direction of the broken pone 101) that is in need of treatment. The PMEF 61 stimulates the healing of the broken bone 101 in the wrist 300.

Elbow Orthotic

Turning now to FIGS. 2 and 3, shown therein is the elbow orthotic 24. The elbow orthotic 24 has an arm component 330, a forearm component 332, and a pivot connector 334 that connect to each of the arm and forearm components 330, 332. Also shown are an upper arm 336, an elbow 338, and a forearm 340 of the patient 100. The elbow orthotic 24 supports the EES 116. The arm component 330 supports a coil assembly 31 having first coil 38*a* and a capacitor 44 and mounted on a first base 49*a*, the pivot connector 334 supports a second coil 38*b* mounted on a second base 49*b*, and the forearm component 332 supports a third coil 38*c* mounted on a third base 49*c*. The third coil 38*c* is wired to the second coil 38*b* with wires commonly designated by reference numeral 312, and the second coil 38*b* is wired to the first coil 38*a* with wires 312, and each is capable of generating a PEMF 51.

The elbow orthotic 24 supports the EES 116 which includes the electronics housing 47 and with the system electronics 60 housed therein. The coil assembly 31 has first and second tabs 45*a*, 45*b* that extend from the first base 49*a* and on which are mounted first and second male snap components 46*a*, 46*b*, respectively. The first and second mail snap components 45*a*, 45*b* are wired to the capacitor 44, and the second male snap component 45*b* is wired to the first coil 38 as shown. Mounted on the electronics housing 47 are first and second female snap components 48*a*, 48*b*, respectively, that are capable of being snap fitted to the first and second male snap components 46*a*, 46*b*, respectively such that the first, second and third coils 38*a*, 38*b* and 38*c* are under the control of the MCU 70. The EES 116 also has an energy source 94 as shown in FIG. 11, such that when the first and second male snap components 46*a*, 46*b* are snapped fitted to the first and second female snap components 48*a*, 48*b* (as indicated by the arrow designated A in FIG. 4) electric power is capable of flowing through the first, second and third coils 38*a*, 38*b*, 38*c* and charging the capacitor 44. When the EES 116 causes current to be supplied to the first, second and third coils 38*a*, 38*b*, and 38*c*, PEMF's 51 are generated that permeate the upper arm 336, the elbow 338, and the forearm 340 of the patient 100 such that they all receive treatment to heal the elbow 338 that is injured or broken.

The above-described elbow orthotic 24 can be used as described above, but in another embodiment shown in FIG. 3, the above-described elbow orthotic 24 with the EES 116 is used in combination with an implantable medical device 130. In this embodiment the implantable medical device 130 is an artificial elbow 341. As shown, the bones 102 the make up the elbow 338 include the humeus bone 342, the ulna bone 344, and the radius bone 346. The artificial elbow 341 includes a humeral component 348 having a bearing 349, an ulnar component 350, and a pin 352 that extends through the bearing 349 and the ulnar component 350, such that the humeral component 348 and the ulnar component 350 are hingedly connected. Artificial elbows and the construction thereof are well known to those having ordinary skill in the art.

In other embodiments the EES 116 may further include repeater coils 54 and device capacitors 44*a* that can be used in a plurality of different medical inserts and spacers to be described presently.

For example, as shown in FIG. 3 an elbow insert 354 is provided and the elbow insert 354 is supported on the bearing 349. In addition, embedded in the elbow insert 354 or in another embodiment supported on the elbow insert 354, is a repeater coil 54 wired to a device capacitor 44*a*. The elbow insert 354 remains in the patient 100 after surgery and is not removed thereafter. When the EES 116 is activated, the first, second and third coils 38*a*, 38*b*, 38*c* generate PMEF's 51 that passes through the humorous bone 342, the ulna bone 344, and radius bone 346 and stimulate these bones to heal. FIG. 14 shows a diagram of the electrical stimulation of an implantable medical device 130.

The PMEF's 51 generated by the first, second and third coils 38*a*, 38*b*, 38*c* also pass through the patient and into the repeater coil 54 such that the repeater coil 54 and the device capacitor 44*a* are activated or powered. In response to being powered by the first, second and third coil assemblies 38*a*, 38*b*, 38*c* the repeater coil 54 emits a repeater pulsed electromagnetic field 61 that passes directly into the humorous bone 342, the ulna bone 344, and radius bone 346. Together the first, second and third coils 38*a*, 38*b*, 38*c* and the repeater coil 54 form a resonant circuit 224 (a resonant circuit 224 is shown schematically in FIG. 12) wherein the repeater coil 54 functions as described. Resonant circuits are well known to those having ordinary skill in the art and are therefore not described in greater detail herein. When activated, the repeater PMEF 61 passes directly into humorous bone 342, the ulna bone 344, and radius bone 346 to promote bone healing. Thus, this treatment provides for healing by the PEMF's 51 generated by the repeater coil 54, and the first, second and third coils 38*a*, 38*b*, 38*c*. The folded portion 362 of the humeral component 348 shows were the elbow insert 354 is fitted as indicated by the arrow designated C in FIG. 3, it being understood the folded portion 362 is for purposes of illustrating the placement of the elbow insert 354. In other embodiments there is only the only one coil assembly 31 that is supported on the pivot connector 334 that forms a resonant circuit 224 with the elbow 356.

In addition, as shown in FIG. 14 the repeater coils 54 and device capacitors 44a in the elbow insert 354 may also be powered wirelessly by an external wireless power transmitter 90 that is received by the wireless power receiver 91, such that the EES 116 is powered, the biometric sensors 210 are powered, and the coil 38 is powered. The PEMF 51 from the coil 38 powers the repeater coil 54 as described above. Any of the implantable medical devices 130 described herein may be powered in a wireless manner.

Knee Orthotic

Turning now to FIGS. 5 and 6, shown therein is the knee orthotic 28. The knee orthotic 28 has a thigh component 400, a lower leg component 404, and a knee orthotic pivot connector 402 that connects the thigh and lower leg component 404. Also shown are a thigh 406, a knee 408 and a lower leg 410 of the patient 100. The knee orthotic 28 supports the EES 116. The thigh component 400 supports a coil assembly 31 having a first coil 38a and the capacitor 44 supported on a first base 49a, the knee orthotic pivot connector 402 supports a second coil 38b on a second base 49b, and the lower leg component supports a third coil 38c on a third base 49c. The third coil 38c is wired to the second coil 38b with wires 312, and the second coil 38b is wired to the first coil 38a with wires 312, and each is capable of generating a PEMF 51. The first, second, and third coils 38a, 38b, 38c are structurally the same as the previously described coil 38, with the only difference being the size dimension.

The knee orthotic 24 the EES 116 supports the electronics housing 47. The coil assembly 31 has first and second tabs 45a, 45b on which are mounted first and second male snap components 46a, 46b, respectively. The first and second mail snap components 45a, 45b are wired to the capacitor 44, and the second male snap component 45b is wired to the first coil 38 as shown. Mounted on the electronics housing 47 are first and second female snap components 48a, 48b, respectively, that are capable of being snap fitted to the first and second male snap components 46a, 46b, respectively. The EES 116 also has an energy source 94 as shown in FIG. 11, such that when the first and second male snap components 46a, 46b are snapped fitted to the first and second female snap components 48a, 48b (as indicated by the arrow designated A in FIG. 5) electric power is capable of flowing through the first, second and third coils 38a, 38b, 38c and charging the capacitor 44. When the EES 116 causes current to be supplied to the coil assembly 31 the first, second and third coils 38a, 38b, 38c generate PEMF's 51 that that permeate a thigh 406, a knee 408 and a lower leg 410 of the patient 100 such that they all receive treatment to heal the knee 408 that is injured or broken. In other works, the PMEF's 51 stimulate bone healing.

The above-described knee orthotic 28 can be used as described above, but in another embodiment shown in FIG. 6, the knee orthotic 28 with the EES 116 is used in combination with an implantable medical device 130 as shown in FIG. 6, and in this embodiment the implantable medical device 130 is an artificial knee 412. FIG. 6 shows the femur 414 and tibia 416, and the patient's patella or kneecap is not shown. The artificial knee 412 includes a femoral component 418, a knee spacer 420, and a tibial component 422 and wherein the knee spacer 420 is positioned between the femoral component 418 and the tibial component 422. The structure and construction of an artificial knee is well known to those having ordinary skill in the art and therefore is not described in greater detail herein.

The knee spacer 420 provides for support and serves and provides for improved bending of 418 femoral component 418 and the tibial component 422 relative to one another. In addition, embedded or mounted on the knee spacer 420 is repeater coil 54 and device capacitor 44a. The knee spacer 420 is C-shaped as shown. The knee spacer 420 remains in the patient 100 after surgery and is not removed thereafter. When the EES 116 is activated, current is supplied to the first, second and third coils 38a, 38b, 38c, and each generates a PEMF 51 that that passes through the femur 414 and the tibia 416 and stimulates these bones to heal.

The PMEF's 51 generated by the first, second and third coils 38a, 38b, 38c, also pass into the knee spacer 420 and activate the repeater coil 54. In response to being powered, the repeater coil 54 emits a repeater pulsed electromagnetic field 61 (repeater PEMF 61) that passes directly into the femur 414 and tibia 416. Together the first, second and third coils 38a, 38b, 38c and the repeater coil 54 form a resonant circuit 224 (resonant circuit 224 is shown schematically in FIG. 12) wherein repeater coil 54 serves as the repeater. Resonant circuits are well known to those having ordinary skill in the art and are therefore not described in greater detail herein. When activated, the repeater PMEF 61 passes directly into femur 414 and the tibia 416 to promote bone healing. Thus, this treatment provides for healing by the PEMF's 51 generated by the first, second and third coils 38a, 38b, 38c and the repeater PEMF 61 generated by the repeater coil 54 in the knee space 420.

Spine Orthotic

Turning now to FIG. 7, shown therein is a spine orthotic 30. The spine orthotic 30 has a spinal support component 450 that defines a spinal support opening 452, and the spinal support component 450 is sized such that it can be fitted around the lower back 454 of the patient 100. In other embodiments the spinal support component 450 is embodied as a cast. The spinal support component 450 is made a flexible resilient material in one of the embodiments, such that when the patient 100 puts the spinal support component on 450 it forms a compression fit against the low back 454 and thus stays in place, that is, it does not slide off of the patient 100. The spinal support component 450 thus abuts against the lower back 454 where a lumber portion 456 is located.

The spine orthotic 25 supports the EES 116 that is structurally the same as the EES 116 described in connection with the ankle orthotic 22. That is, the EES 116 includes the coil assembly 31 that includes a coil 38 and a capacitor 44 forming a LC circuit 43, supported on a base 49. The EES 116 also includes an electronics housing 47. The coil assembly 31 is mounted on the spinal support component 450 as shown in FIG. 7, and the coil assembly 31 has first and second tabs 45a, 45b on which are mounted first and second male snap components 46a, 46b, respectively. The first and second mail snap components 45a, 45b are wired to the capacitor 44, and the second male snap component 45b is wired to the first coil 38 as shown. Mounted on the electronics housing 47 are first and second female snap components 48a, 48b, respectively, that are capable of being snap fitted to the first and second male snap components 46a, 46b, respectively, and when snap fitted the coil 38 is capable of being controlled by the MCU 70. The EES 116 also has an energy source 94 as shown in FIG. 11, such that when the first and second male snap components 46a, 46b are snapped fitted to the first and second female snap components 48a, 48b (as indicated by the arrow designated A in FIG. 7) electric power is capable of flowing through the coil 38 and charging the capacitor 44. When the EES 116 causes current to be supplied to the coil 38 a PEMF 51 is generated that permeates the lumbar portion 456 of the spine 458 of the patient 100 at the location where he or she has a wound area (indicated by dashed reference line 108 in FIG. 7), and permeates fractured or broken bone 101, and in this case lumbar vertebrae L1 and L2 560, 562 (see FIG. 8) that are in need of treatment. In other words, the PMEF 51 stimulates the healing of the broken bone bones 101 in the spinal column 458.

The above-described spine orthotic 30 can be used as described above, but in another embodiment shown in FIG. 8, the spine orthotic 30 with the EES 116 is used in combination with an implantable medical device 130 as shown in FIG. 8, and in this embodiment the implantable medical device 130 is a spine insert 460. FIG. 8 depicts a portion of the spinal column 458 showing the lumbar portion 456 of the spinal column 458. Shown are lumbar vertebrae L1, L2, L3 designated 474, 476, 478 respectively, with lumbar vertebrae L5 474 supported on the sacrum 480. The spine insert 460 is fitted between the lumbar vertebrae L1 and L2 designated 474, 476. It is pointed out that a portion of the second lumbar vertebrae L2 562 is shown in dashed line. In addition, not shown are the other components that are typically used in connection with installing the spine insert 460 in the spine, for example screws, rods, hooks, and the like for the sake of clarity, it being understood that all of these other components are well known to those having ordinary skill in the art.

The spine insert 460 has a cylindrical shaped body 462 having opposed inner and outer body surfaces 464, 466, and the cylindrical shaped body 462 defines a spine insert opening 468. The spine insert 460 has a repeater coil 54 that is cylindrical or circular shaped and wired to a device capacitor 44a is mounted thereon or embedded therein, for example they may be mounted on the inner or outer body surfaces 464, 466. The spine insert opening 468 is filled with material, for example cadaver bone as is well known to those having ordinary skill in the art. The spine insert 460 remains in the patient 100 after surgery and is not removed thereafter. When the EES 116 is activated, current supplied to the coil assembly 31 generates a PEMF 51 that passes through the patient 100 and into the lumbar vertebrae L1, L2 designated 474, 476 and stimulates these bones to heal.

The PMEF's 51 generated by the coil assembly 31 pass through the repeater coil 54 and capacitor 44, the repeater coil 44 is activated or powered. In response to being powered by the coil assembly 31, the repeater coil 54 emits a repeater pulsed electromagnetic field 61 (repeater PEMF 61) that passes directly into the lumbar vertebrae L1, L2 designated 474, 476. Together coil assembly 31 and repeater coil 54 form the resonant circuit 224 (resonant circuit 224 is shown schematically in FIG. 12). When activated, the repeater PMEF 61 passes directly into the lumbar vertebrae L1, L2 designated 474, 476 to promote bone healing. Thus, this treatment provides for healing by the PEMF's 51 generated by the coil assembly 31 and the repeater PEMF 61 generated by the repeater coil 54.

Hip Orthotic

As shown in FIG. 9 there is the hip orthotic 40 having a waist portion 502 and a leg thigh portion 504. The waist portion 502 defines a waist opening 506 and the waist portion 502 mergers with the leg thigh portion 504. The leg thigh portion 504 defines a thigh opening 508. FIG. 9 shows the hip orthotic 40 worn by the patient 100 with the thigh 406 of the patient 100 extending through the thigh opening 508, and the waist portion 506 surrounding the patient 100 and supported on the waist 510 of the patient 100. The hip orthotic 40 may be made of a flexible resilient material or may be in the form of a hip cast 511. As shown, the patient 100 is wearing underwear 500 and the hip orthotic 40 is placed over the underwear 500.

The waist portion 502 supports a coil assembly 31 having a first coil 38a and capacitor 44 mounted on a first base 49a, and a second coil 38b is supported on a second base 49b and is mounted on the leg thigh portion 504. The second coil 38b is wired to the first coil 38a with wires 312, and each is capable of generating a PEMF 51.

The hip orthotic 40 supports the EES 116 which includes the electronics housing 47. The coil assembly 31 has first and second tabs 45a, 45b on which are mounted first and second male snap components 46a, 46b, respectively. The first and second mail snap components 45a, 45b are wired to the capacitor 44, and the second male snap component 45b is wired to the first coil 38. Mounted on the electronics housing 47 are first and second female snap components 48a, 48b, respectively, that are capable of being snap fitted to the first and second male snap components 46a, 46b, respectively. The EES 116 also has an energy source 94 as shown in FIG. 11, such that when the first and second male snap components 46a, 46b are snapped fitted to the first and second female snap components 48a, 48b electric power is capable of flowing through the first and second coils 38a, 38b and charging the capacitor 44. When the EES 116 causes current to be supplied to the first and second coils 38a, 38b, PEMF's 51 are generated that permeate hip joint 520 (shown in FIG. 11) and hip bone 522, the femur 414 and the hip joint 520, such that they receive treatment. In other works, the PMEF's 61 stimulate bone healing.

Figure 10:
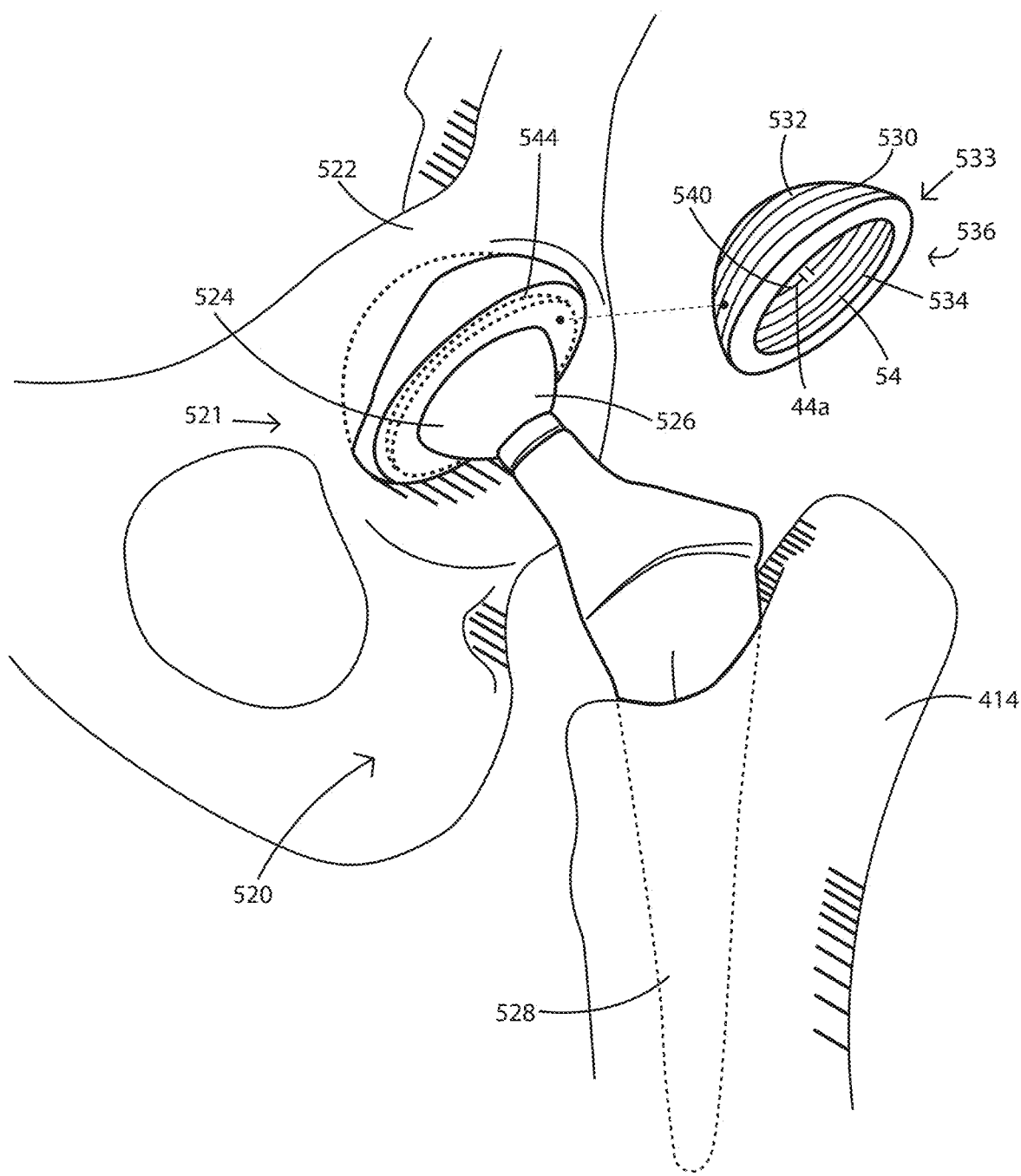
FIG. 10 is a front view showing an implantable hip insert having a repeater coil that is conical shaped wired to a device capacitor and that is inductively powered by the EES shown in FIG. 9.

The above-described hip orthotic 40 can be used as described above, but in another embodiment shown in 10, the hip orthotic 40 with the EES 116 is used in combination with an implantable medical device 130 as shown in FIG. 10, and in this embodiment the implantable medical device 130 is an artificial hip 524. As shown, the bones 102 the make up the hip 521 include hip bone 522 and the femur 414. The artificial hip 524 has a femoral head 526 supported on a femoral arm 528, and femoral head 526 is received in an artificial socket 544 that is supported by the hip bone 522. The femoral arm 528 extends into the femur 414. Artificial hips 524 and the construction thereof are well known to those having ordinary skill in the art.

A hip insert 530 is provided and the hip insert 530 is generally shaped like a half sphere and has a convex outer surface 532 and concave inner surface 534, and defines a femoral head socket 536 sized to receive the femoral head 526 therein. Embedded in the hip insert 530 are a repeater coil 54 that is conical shaped 533, and a device capacitor 44a. In other embodiments the repeater coil 54 may be disposed on the convex outer surface 532 or concave inner surface 534. The hip insert 530 with repeater coil 54 and capacitor 44 remains in the patient 100 after surgery and is not removed thereafter. When the EES 116 is activated, the first and second coils 38a, 38b generate PMEF's 51 that passes through hip bone 522 and femur 414 and stimulate these bones to heal.

The PMEF's 51 generated by the first and second coils 38a, 38b, pass through the patient 100 and activate the repeater coil 54 and capacitor 44. In response to being powered by the first and second coils 38a, 38b the repeater coil 54 emits a repeater pulsed electromagnetic field 61 that passes directly into the femur 414 and hip bone 522. Together the first and second coils 38a, 38b and the repeater coil 54 form a resonant circuit 224 (a resonant circuit 224 is shown schematically in FIG. 12) wherein the repeater coil 54 serves as the repeater. Resonant circuits are well known to those having ordinary skill in the art and are therefore not described in greater detail herein. When activated, the repeater PMEF 61 passes directly into femur 414 and hip bone 522 to promote bone healing. Thus, this treatment provides for healing by the PEMF's 51 generated by the first and second coils 38a, 38b and the repeated PEMF 61 generated by the coil 54.

It is pointed out that the therapy and treatments described herein allows for an increase/in bone healing by a factor of up to approximately 60% or more. The patient 100 is prescribed to wear the orthotic device 20 depending on the severity of the injury as well as the location of the break.

The patient will undergo treatment from approximately two (2) to about nine (9) hours per day. It is pointed out that the MCU 70 unit is programmable from 0 to twelve (12) hours to provide for the continuous operation thereof. The above described device will be used for up to about nine (9) months after the injury.

In addition, other embodiments the orthotic 20 may be made from smart fabric technology that provides for fabric 28 (shown in FIG. 4) that is breathable and sustainable while at the same time securely holds in place the broken bone 11 and the bones surrounding and the broken bone 11. The fabric 28 is capable of supporting aerating and oxygenating the wound area 108, because of the breathable fabric and doesn't block the normal function of the bandage.

Capacitively and Inductively Coupled Electrical Stimulation

It is noted that either a coils 38 or repeater coils 54 are used in conjunction with the support 20 for bone healing purposes. The bone regeneration system 10 presented here allows the inductively coupled (IC) coil 38 for bone healing purposes. The EES 116 on the support 20 includes a PEMF drive circuit 52 (FIG. 11) for the coils 38.

The inductively coupled (IC) stimulation, which is non-invasive, produces electrical fields in bone 107 with varying or pulsed electromagnetic fields (hence this technique is referred to as PEMF 51). As described above, the PEMF 51 can be produced by a single or multiple coils 38 that are driven by an external power source. The outcome is a secondary electrical field produced in the bone 107 as is well known by one having ordinary skill in the art. Both the characteristics of the applied magnetic fields and the biological properties of the tissues and bone 107 influence the induced secondary field. In practice, the configurations of the applied magnetic fields vary by amplitude, frequency single pulse or pulse burst (a serious of pulses with frequencies of 1 to 100 bursts/second) and more generally the excitation wave form. Varying configurations are capable of producing magnetic fields of 0.1-20 G, which have produced voltage gradients of 1-100 mV/cm.

Multiple Sensor Selection

One or more biometric sensors 210 can be used to monitor a patient 100 in the healing process. The patient's 100 attendant (not shown) can choose which sensors 210 to monitor through the user interface, for example the user smart device 110, that is in electronic communication with the MCU 70. The MCU 70 sets the appropriate amplifier gain for each sensor 210 and selects the analog multiplexer channel to be read. The A/D converts the analog signal to a digital format which can be processed by the MCU 70. Any part of the above mentioned circuitry can be part of the micro-controllers circuitry. The MCU 70 logs the data, for example the biometric sensor data 212 that can be viewed real time and/or stored over a period of time.

User Interface and the Cloud

This bone regeneration system 10 also includes a wireless transceiver 80 (FIG. 11) that can communicate via bluetooth LE or direct wifi with a users smart device. The user's smart device 110 forms the connection with the cloud and the patient information in the form of biometric sensor data 212 can be shared amongst Health Care providers (not shown) in a known manner.

It will be appreciated by those skilled in the art that while the bone regeneration system 10 has been described in detail herein, the invention is not necessarily so limited and other examples, embodiments, uses, modifications, and departures from the embodiments, examples, uses, and modifications may be made without departing from the process and all such embodiments are intended to be within the scope and spirit of the appended claims.

What is claimed:

1. A bone regeneration system for healing a bone of a patient, the bone regeneration system comprising:
    a support for supporting the bone to be healed;
    an electrical stimulation system having a housing and the housing is mounted on the support, and the electrical stimulation system includes a microcontroller that is programmable and located in the housing, and a coil assembly that is under the control of the microcontroller, and an energy source disposed in the housing, and the coil assembly is mounted on the support;
    wherein the electrical stimulation system further includes a system regulator, a pulsed electromagnetic field drive circuit, a pulsed electromagnetic field voltage regulator, and a system voltage regulator that are wired to the microcontroller, and a user interface to enable programming of the microcontroller to produce a desired electrical output signal to drive the coil in order to promote mote bone healing;
    wherein the coil assembly is powered by the power source and the coil assembly is capable of generating a pulsed electromagnetic field such that upon being activated the pulsed electromagnetic field penetrates the bone and accelerates the healing of the bone; and
    wherein the coil assembly further includes a base, and a coil and capacitor are mounted on the base, and coil is wired to the capacitor, and first and second tabs extend from the base, and the first tab supports a first male snap component and the second tab supports a second male snap component that are wired to the capacitor, and first and second female snap components are mounted on the housing and the first and second male snap components are capable of being snap fitted to the first and second female snap components, such that when snap fitted together current can be delivered from the energy source coil such that the pulsed electromagnetic field is generated by the coil.

2. The bone regeneration system according to claim 1 wherein the support is selected from the group consisting of:
    an ankle orthotic;
    an elbow orthotic;
    a wrist orthotic;
    a knee orthotic;
    a spine orthotic; and, a hip orthotic.

3. The bone regeneration system according to claim 1 further including an implantable medical device and wherein the implantable medical device is capable of being implanted into the patient, and the implantable medical device supports a device capacitor wired to a repeater coil, such that when the repeater coil is activated in response to a pulsed electromagnet field generated by the coil, the repeater coil emits a pulsed electromagnetic field directly into the bone of the patient such that the bone is stimulated to heal by both the pulsed electromagnetic fields emitted from the coil and emitted from repeater coil.

4. The bone regeneration system according to claim 1 further including an elbow orthotic having an arm component that supports a coil assembly that supports a first coil wired to a capacitor, and first and second tabs extend from the base, and the first tab supports a first male snap component and the second tab supports a second male snap component that are wired to the capacitor, and first and second female snap components are mounted on the housing and the first and second male snap components are capable of being snap fitted to the first and second female snap components, such that when snap fitted together current can be delivered from the energy source coil such that the pulsed electromagnetic field is generated, and further including an artificial elbow having an elbow insert having a repeater coil wired to a device capacitor such that when the coil of the coil assembly is activated it generates a pulsed electromagnetic field that activates the repeater coil such that the repeater coil emits a repeated coil pulsed electromagnetic field that permeates an elbow of the patient to accelerate bone healing.

5. The bone regeneration system according to claim 4 further wherein the elbow orthotic includes a pivot component and a forearm component and the pivot component is pivotally connected to the forearm component and the arm component, and a second coil is mounted on the pivot component and a third coil is mounted on the forearm component and the third coil is wired to the second coil and the second coil is wired to the first coil such that when powered the first, second, third and repeater coils generate pulsed electromagnetic fields to promote bone healing.

6. The bone regeneration system according to claim 1 further including an knee orthotic having a thigh component that supports a coil assembly that supports a first coil wired to a capacitor, and first and second tabs extend from the base, and the first tab supports a first male snap component and the second tab supports a second male snap component that are wired to the capacitor, and first and second female snap components are mounted on the housing and the first and second male snap components are capable of being snap fitted to the first and second female snap components, such that when snap fitted together current can be delivered from the energy source coil such that the pulsed electromagnetic field is generated, and further including knee spacer having a repeater coil wired to a device capacitor such that when the coil of the coil assembly is activated the coil generates a pulsed electromagnetic field that activates the repeater coil such that the repeater coil emits a repeated coil pulsed electromagnetic field that permeates a knee of the patient to accelerate bone healing.

7. The bone regeneration system according to claim 6 further wherein the knee orthotic includes a knee orthotic pivot connector and a lower leg components and the pivot component is connected to the thigh component and lower leg component and a second coil is mounted on the pivot component and a third coil is mounted on the forearm component, and the third coil is wired to the second coil and the second coil is wired to the first coil such that when powered the first, second, third and repeater coils generate pulsed electromagnetic fields to promote bone healing.

8. The bone regeneration system according to claim 1 further including an spine orthotic having a spinal support component that supports a coil assembly having a coil wired to a capacitor, and first and second tabs extend from the base, and the first tab supports a first male snap component and the second tab supports a second male snap component that are wired to the capacitor, and first and second female snap components are mounted on the housing and the first and second male snap components are capable of being snap fitted to the first and second female snap components, such that when snap fitted together current can be delivered from the energy source coil such that the pulsed electromagnetic field is generated, and further including spine insert having a repeater coil wired to a device capacitor such that when the coil when the coil of the coil assembly is activated the coil generates a pulsed electromagnetic field that activates the repeater coil such that the repeater coil emits a repeated coil pulsed electromagnetic field that permeates a spine of the patient to accelerate bone healing.

9. The bone regeneration system according to claim 8 further wherein the spine insert has a cylindrical shaped body and defines a spine insert opening and the repeater coil is supported by the cylindrical shaped.

10. The bone regeneration system according to claim 1 further including a hip orthotic having a waist portion from which extends a leg thigh portion and the hip portion supports a coil assembly that supports a first coil wired to a capacitor, and first and second tabs extend from the base, and the first tab supports a first male snap component and the second tab supports a second male snap component that are wired to the capacitor, and first and second female snap components are mounted on the housing and the first and second male snap components are capable of being snap fitted to the first and second female snap components, such that when snap fitted together current can be delivered from the energy source coil such that the pulsed electromagnetic field is generated, and further including a hip insert having a repeater coil wired to a device capacitor such that when the coil of the coil assembly is activated the coil generates a pulsed electromagnetic field that activates the repeater coil such that the repeater coil emits a repeated coil pulsed electromagnetic field that permeates a hip of the patient to accelerate bone healing.

11. The bone regeneration system according to claim 10 further wherein the leg thigh portion of the hip orthotic includes a second coil that is mounted on the leg thigh portion and wherein the leg thigh portion coil is wired to the first coil such that when powered the first and second coils and the repeater coil generate pulsed electromagnetic fields to promote bone healing.

12. The bone regeneration system according to claim 11 wherein the hip insert has a convex outer surface and a concave inner surface such that it has a conical shape and the coil has a shape that mimics the shape of the hip insert.

13. The bone regeneration system according to claim 1 further including a wrist orthotic having a hand portion that supports a coil assembly having a coil wired to a capacitor, and first and second tabs extend from the base, and the first tab supports a first male snap component and the second tab supports a second male snap component that are wired to the capacitor, and first and second female snap components are mounted on the housing and the first and second male snap components are capable of being snap fitted to the first and second female snap components, such that when snap fitted together current can be delivered from the energy source coil such that the pulsed electromagnetic field is generated, and further including a spine insert having a repeater coil wired to a device capacitor such that when the coil of the coil assembly is activated the coil generates a pulsed electromagnetic field that activates the repeater coil such the repeater coil emits a repeated coil pulsed electromagnetic field that permeates a spine of the patient to accelerate bone healing.

14. The bone regeneration system according to claim 1 further including an active bandage having a padding layer with opposed first and second padding surfaces and wherein the housing is capable of being adhered to first padding surface and the second padding surface is capable of being adhered to skin, the padding layer supports the housing and a coil assembly having a coil wired to a capacitor, and the padding supports a first male snap component and a second male snap component that are wired to the capacitor, and first and second female snap components are mounted on the housing and the first and second male snap components are capable of being snap fitted to the first and second female snap components, such that when snap fitted together current can be delivered from the coil such that the pulsed electromagnetic field is generated that permeates a bone of the patient to accelerate bone healing.

15. The bone regeneration system according to claim 14 wherein the electrical stimulation system further includes sensors that are supported on the skin and are under the control of and communication with the microcontroller and are placed on the skin and wherein the sensors detect and gather biometric sensor data, including pH level data, pressure level data, temperature data, moisture data, humidity data.

16. The bone regeneration system according to claim 14 further including an implantable medical device that is capable of being implanted into the patient, and the implantable medical device supports a device capacitor wired to a repeater coil, such that when the repeater coil is activated in response to a pulsed electromagnet field generated by the coil supported by the padding the repeater coil emits a pulsed electromagnetic field directly into the bone of the patient such that the bone is stimulated to heal by both the pulsed electromagnetic fields emitted from the coil and emitted from the repeater coil.

17. A bone regeneration system for healing a bone of a patient, the bone regeneration system comprising:
 a support for supporting the bone to be healed;
 an electrical stimulation system having a housing and the housing is mounted on the support, and the electrical stimulation system includes a microcontroller that is programmable and located in the housing, and a coil assembly that is under the control of the microcontroller, and includes a system regulator, a pulsed electromagnetic field drive circuit, a pulsed electromagnetic field voltage regulator, and a system voltage regulator that are wired to the microcontroller, and a user interface to enable programming of the microcontroller to produce a desired electrical output signal to drive the coil in order to promote mote bone healing;
 a portable device having a power source and having a wireless power transmitter that is powered by the power source and that is capable of emitting a resonantly tuned frequency that is received by a wireless power receiver that is mounted on the support and that is wired to the electrical stimulation system such that the electrical stimulation system is powered wirelessly;
 wherein a coil assembly is mounted on the support and the coil assembly and is powered by power received by the wireless power receiver and wherein when powered the coil assembly is powered it is capable of generating a pulsed electromagnetic field that penetrates the bone and accelerates the healing of the bone; and
 further including an implantable medical device that is capable of being implanted into the patient, and the implantable medical device supports a device capacitor wired to a repeater coil wired to a capacitor, such that when the repeater coil is activated in response to a pulsed electromagnet field generated by the coil supported on the support the repeater coil emits a pulsed electromagnetic field directly into the bone of the patient such that the bone is stimulated to heal by both the pulsed electromagnetic fields emitted from the coil and emitted from repeater coil.

18. A method for healing a bone with a bone regeneration system comprising the acts of:
 providing a support for supporting the bone to be healed;
 providing an electrical stimulation system having a housing and mounting the housing on the support, and providing the electrical stimulation system with a microcontroller that is programmable and positioning the microcontroller in the housing, and providing a coil assembly that is under the control of the microcontroller, and placing an energy source in the housing, and mounting the coil assembly on the support;
 providing the electrical stimulation system with a system regulator, a pulsed electromagnetic field drive circuit, a pulsed electromagnetic field voltage regulator, and a system voltage regulator that are wired to the microcontroller, and providing the electrical stimulation system with an interface to enable programming of the microcontroller to produce a desired electrical output signal to drive the coil in order to promote mote bone healing;
 providing the coil assembly with a base and mounting a coil wired to a capacitor on the base, and providing first and second tabs that are connected to and extend from the base, and mounting a first male snap component on the first tab, and mounting a second male snap component on the second tab and wiring the capacitor to the first and second snap components, and mounting first and second female snap components on the housing and the first and second male snap components are capable of being snap fitted to the first and second female snap components, such that when snap fitted together current can be delivered from the energy source coil such that the pulsed electromagnetic field is generated by the coil; and
 powering the coil assembly with the energy source such that the coil assembly generates a pulsed electromagnetic field such that upon being activated the pulsed electromagnetic field penetrates the bone and accelerates the healing of the bone.

19. The method for healing a bone with a bone regeneration system according to claim 18 including the further act of selecting the support from the group consisting of:
 an ankle orthotic;
 an elbow orthotic;
 a wrist orthotic;
 a hip orthotic;
 a knee orthotic; and,
 a spine orthotic.

20. The method for healing a bone with a bone regeneration system according to claim 18 including the further acts of providing an implantable medical device and supporting a device capacitor wired to a repeater coil on the implantable medical device, such that when the repeater coil is activated in response to a pulsed electromagnet field generated by the coil the repeater coil emits a pulsed electromagnetic field directly into the bone such the bone is stimulated to heal by both the pulsed electromagnetic fields emitted from the coil and emitted from repeater coil.

21. The method for healing a bone with a bone regeneration system according to claim 20 wherein the implantable medical device having the repeater coil and device capacitor is selected from the group of implantable medical devices comprising:

an elbow insert;
a knee spacer;
a spine insert, and;
a hip insert.

* * * * *